(12) United States Patent
Yokoi et al.

(10) Patent No.: US 9,702,796 B2
(45) Date of Patent: Jul. 11, 2017

(54) ISOLATOR

(71) Applicant: Panasonic Healthcare Co., Ltd., Ehime (JP)

(72) Inventors: Yasuhiko Yokoi, Ehime (JP); Koichi Kobayashi, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 360 days.

(21) Appl. No.: 14/460,920

(22) Filed: Aug. 15, 2014

(65) Prior Publication Data

US 2014/0356942 A1 Dec. 4, 2014

Related U.S. Application Data

(63) Continuation of application No. PCT/JP2013/053056, filed on Feb. 8, 2013.

(30) Foreign Application Priority Data

Feb. 21, 2012 (JP) ................................ 2012-035628

(51) Int. Cl.
| | |
|---|---|
| *C12M 1/34* | (2006.01) |
| *G01N 1/34* | (2006.01) |
| *C12M 1/12* | (2006.01) |
| *A61L 2/20* | (2006.01) |
| *F24F 3/16* | (2006.01) |

(52) U.S. Cl.
CPC ............. *G01N 1/34* (2013.01); *C12M 37/00* (2013.01); *A61L 2/20* (2013.01); *F24F 3/1607* (2013.01)

(58) Field of Classification Search
CPC ............ B25H 1/12; B25H 1/20; C12M 37/00; C12M 41/14; G01N 1/34
See application file for complete search history.

(56) References Cited

U.S. PATENT DOCUMENTS

2004/0168341 A1* 9/2004 Petersen .................. B25J 21/02
34/402

FOREIGN PATENT DOCUMENTS

| EP | 1 997 876 A1 | 12/2008 | |
|---|---|---|---|
| GB | 2276088 A * | 9/1994 | ............. A01K 1/031 |
| JP | 58-67536 U | 5/1983 | |

(Continued)

OTHER PUBLICATIONS

Extended European Search Report issued in Application No. 13752108.4 dated Oct. 15, 2015.

(Continued)

*Primary Examiner* — William H Beisner
(74) *Attorney, Agent, or Firm* — McDermott Will & Emery LLP

(57) ABSTRACT

An isolator includes: a chamber including a working chamber in which a work is performed by a worker, and a storage chamber provided under the working chamber in communication with an opening formed in a bottom plate of the working chamber, the chamber being configured to isolate the working chamber and the storage chamber from an exterior while in a state where airtightness is maintained; and a lifting device configured to support, in the storage chamber, an experimental device to be used in the working chamber, the lifting device being capable of lifting and lowering the experimental device from the storage chamber to the working chamber and from the working chamber to the storage chamber.

21 Claims, 14 Drawing Sheets

(56) References Cited

FOREIGN PATENT DOCUMENTS

| | | |
|---|---|---|
| JP | 2007-263449 A | 10/2007 |
| JP | 2009-225742 A | 10/2009 |
| JP | 2011-177091 A | 9/2011 |

OTHER PUBLICATIONS

International Search Report and Written Opinion issued in International Application No. PCT/JP2013/053056 dated May 7, 2013, with partial English translation.

* cited by examiner

ISOLATOR

CROSS-REFERENCE TO RELATED APPLICATION

This is a continuation application of International Patent Application No. PCT/JP2013/053056 filed Feb. 8, 2013, which claims the benefit of priority to Japanese Patent Application No. 2012-035628 filed Feb. 21, 2012. The full contents of the International Patent Application are incorporated herein by reference.

BACKGROUND

Technical Field

The present disclosure relates to an isolator.

Description of the Related Art

Japanese Patent Application Laid-open Publication No. 2011-177091 discloses a chamber including a working chamber for, for example, performing work such as observation of a cultured cell and the like.

For example, changes in the observation target such as a cultured cell and the like over time may be observed, using an observation device in the working chamber of the chamber disclosed in the above publication. On such an occasion, work space may be decreased due to the observation device being housed in the chamber.

SUMMARY

An isolator according to an aspect of the present disclosure, includes: a chamber including a working chamber in which work is performed by a worker, and a storage chamber provided under the working chamber in such a manner as to communicate with an opening formed in a bottom plate of the working chamber, the chamber being configured to isolate the working chamber and the storage chamber from an exterior in a state where airtightness is maintained; and a lifting device configured to support, in the storage chamber, an experimental device to be used in the working chamber, the lifting device being capable of lifting and lowering the experimental device from the storage chamber to the working chamber and from the working chamber to the storage chamber.

Other features of the present disclosure will become apparent from descriptions of the present specification and of the accompanying drawings.

DETAILED DESCRIPTION

At least the following details will become apparent from descriptions of the present specification and of the accompanying drawings.

First Embodiment

===Isolator===

Figure 1:
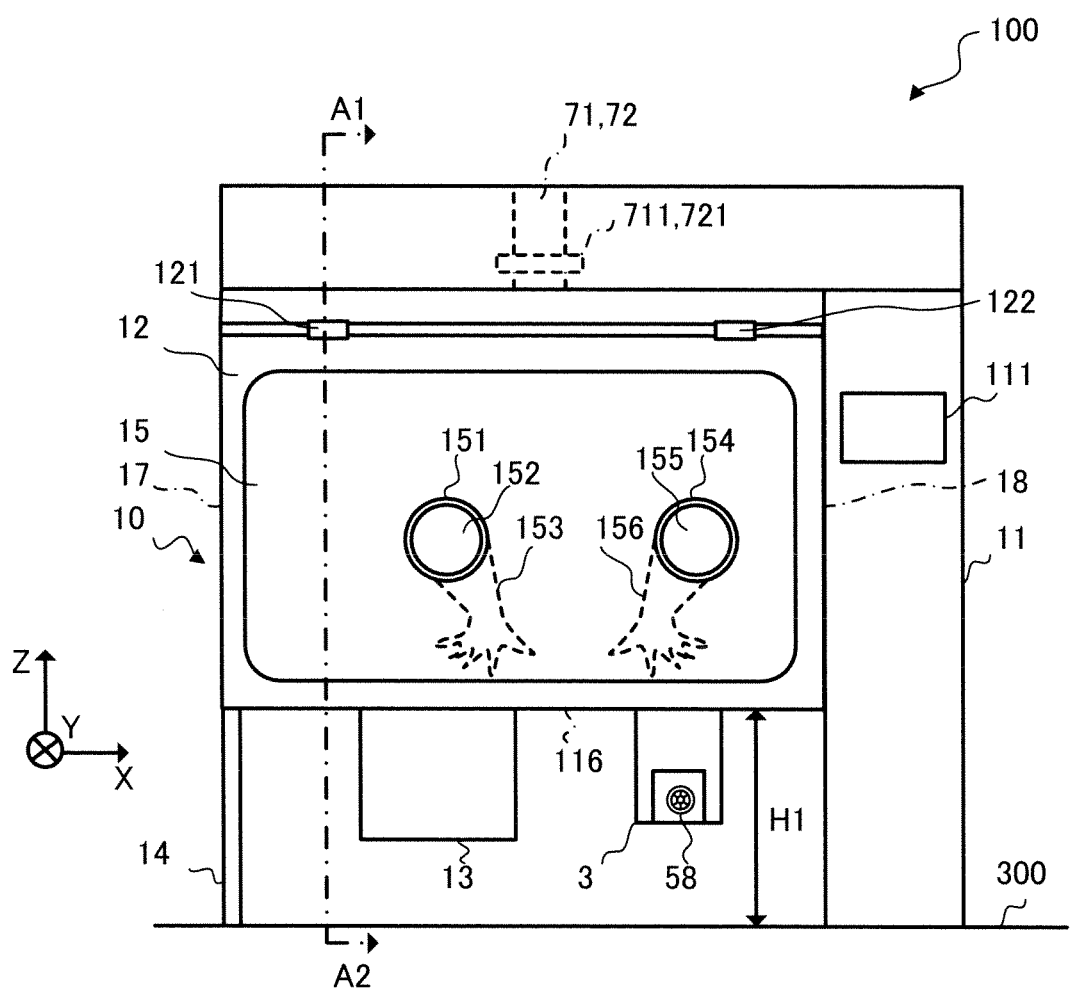
FIG. 1 is an exemplary front view illustrating an isolator according to a first embodiment of the present disclosure.

Hereinafter, an isolator according to an embodiment of the present disclosure will be described with reference to FIG. 1. FIG. 1 is a front view illustrating the isolator according to an embodiment of the present disclosure.

The isolator 100 is a device for performing work, such as cell culture, cell operation, cell observation, and the like, in a decontaminated environment. Note that decontamination is assumed to represent bringing a state closer to an aseptic state by killing microorganisms, cells, and the like. The isolator 100 is provided to stand, for example, on an installation surface 300 of a laboratory or the like. The isolator 100 includes a chamber 10, a body 11, and legs 14. Note that, in an embodiment of the present disclosure, the Z-axis is an axis along a perpendicular direction in which the isolator 100 is provided to stand, wherein a direction toward an upper side is referred to as the +Z direction, and a direction toward a lower side (downward) is referred to as the −Z direction. The Y-axis is an axis along a direction orthogonal to the front surface and the back surface of the isolator 100, wherein a direction from the front surface, provided with openings 152, 155 for performing work in the interior of the chamber 10, toward the back surface opposite to the front surface is referred to as the +Y direction, and a direction from the back surface toward the front surface is referred to as the −Y direction. The X-axis is an axis along a direction orthogonal to side plates 17, 18 of the chamber 10, wherein a direction from the side plate 18 connected to the body 11 in the chamber 10 toward the side plate 17 opposite to the side plate 18 is referred to as the −X direction, and a direction from the side plate 17 to the side plate 18 is referred to as the +X direction.

The chamber 10 includes a working chamber 16 (FIG. 2) where bacterial invasion from the exterior is restrained. Note that the details of the chamber 10 will be described later.

The body 11 is provided with, for example, a control device 8 (FIG. 4) configured to control the isolator 100. Note that the details of the control device 8 will be described later. The body 11 is formed, for example, in a substantially rectangular parallelepiped shape and is provided to stand on the installation surface 300. A touch panel 111, through which information is inputted to the control device 8, is provided on the front face of the body 11. The body 11, together with the legs 14, supports the chamber 10 such that a height of the bottom plate 116 of the chamber 10 from the installation surface 300 is set to a predetermined height H1. Note that the details of the predetermined height H1 will be described later. The side plate 18 of the chamber 10 is, for example, welded to a side surface on the chamber 10 side of the body 11.

The legs 14 are, for example, two support members that support the chamber 10, as described above. The legs 14 are mounted to a corner on the front side (−Y) and a corner on the back side (−Y) of the bottom plate 116 of the chamber 10.

===Chamber===

Figure 2:
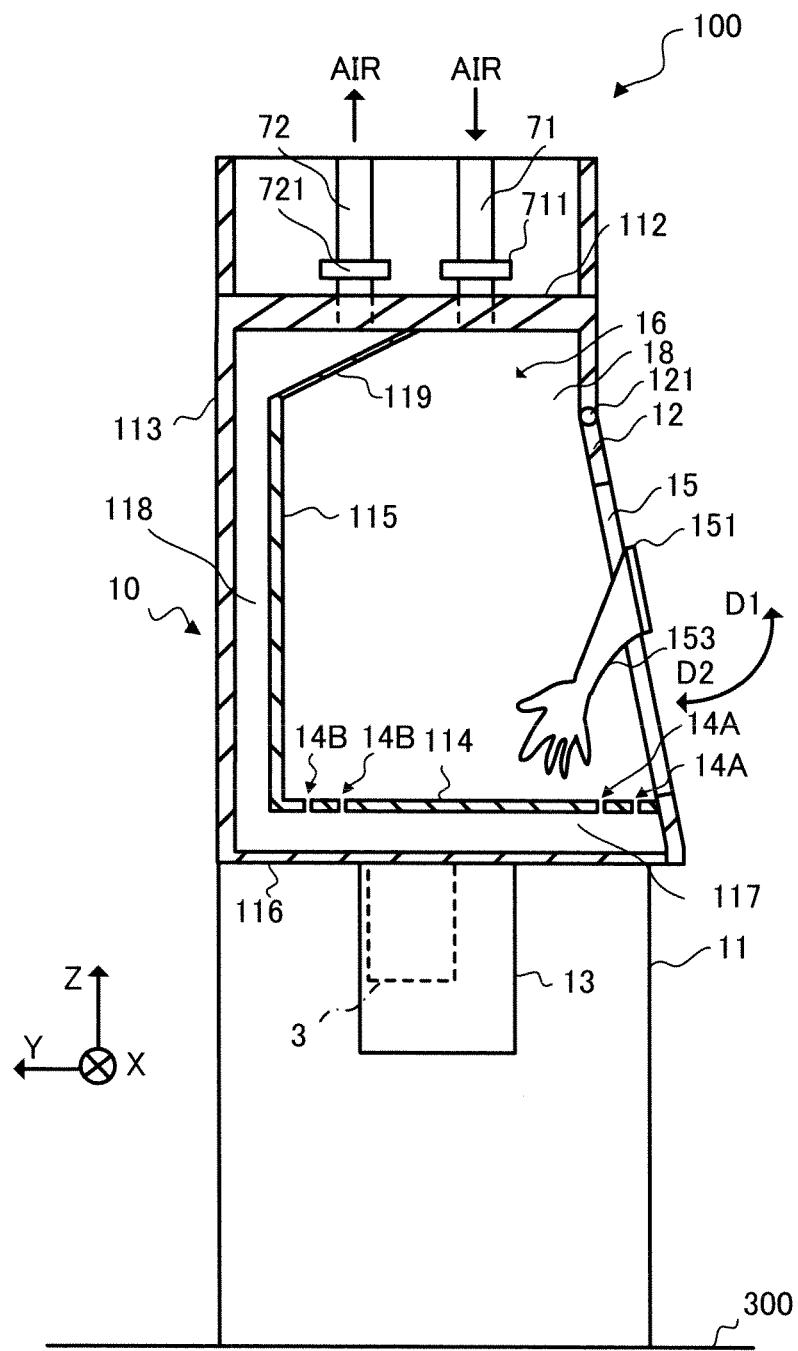
FIG. 2 is an exemplary cross-sectional view illustrating an isolator according to a first embodiment of the present disclosure.

Hereinafter, the chamber according to an embodiment of the present disclosure will be described with reference to FIGS. 1 and 2. FIG. 2 is a cross-sectional view of the isolator in an embodiment of the present disclosure when viewed from the section line A1-A2 toward the +X side in FIG. 1.

The chamber 10 is, for example, a metal device formed in a substantially rectangular parallelepiped shape. The chamber 10 is a hollow structure such that the working chamber 16 can be provided in the interior thereof. Note that the details of the working chamber 16 will be described later. The interior of the chamber 10 is isolated from the exterior and maintained in an airtight state, so that bacterial invasion from the exterior of the chamber 10 is restrained. Note that the interior and the exterior of the chamber 10 are separated, for example, by the bottom plate 116, a back plate 113, a top plate 112, a door 12, and the side plates 17, 18, which are made of metal and formed in a substantially rectangular shape.

The chamber 10 includes the door 12, a centrifuge 13, and a storage chamber 3.

The door 12 is provided, for example, on the front surface (−Y) of the chamber 10. The door 12 is mounted to the chamber 10, for example, in such a manner as to be pivotally moved in a direction D1 or a direction D2 (FIG. 2) about a rotating shaft along the X-axis of hinges 121, 122 that are mounted on the upper side of the door 12. Note that, for example, a seal material such as rubber packing or the like is assumed to be provided on the edge of the door 12, so that the interior of the chamber 10 is maintained airtight when the door 12 is closed by being pivotally moved in the direction D2 about the rotating shaft along the X-axis of the hinges 121, 122. That is, when the door 12 is closed, the door 12 performs a function as a partition plate for separating the interior of the chamber 10 from the exterior while maintaining the interior of the chamber 10 in an airtight state.

The door 12 is provided with a transparent plate 15 made of, for example, resin and the like, such that the interior of the chamber 10 can be viewed from the exterior of the chamber 10.

The transparent plate 15 is provided with, for example, two gloves 153, 156 extending into the working chamber 16.

The gloves 153, 156 are used, for example, when a worker, outside of the working chamber 16, who performs cell culture, cell operation, cell observation, and the like (hereinafter, referred to as "work such as cell culture"), performs work such as cell culture in the working chamber 16. The gloves 153, 156 are mounted to frames 151, 154 of the openings 152, 155, respectively, so that a worker can perform work such as cell culture by inserting his/her hands from the openings 152, 155 of the transparent plate 15 into the working chamber 16, while the interior of the working chamber 16 is maintained in an airtight state.

The centrifuge 13 is a device used to separate elements, for example, from cell suspension which is a mixture of solids such as cells and a plurality of liquids of different densities. The centrifuge 13 is provided in such a manner as to protrude downward (−Z) from the bottom plate 116.

Figure 5:
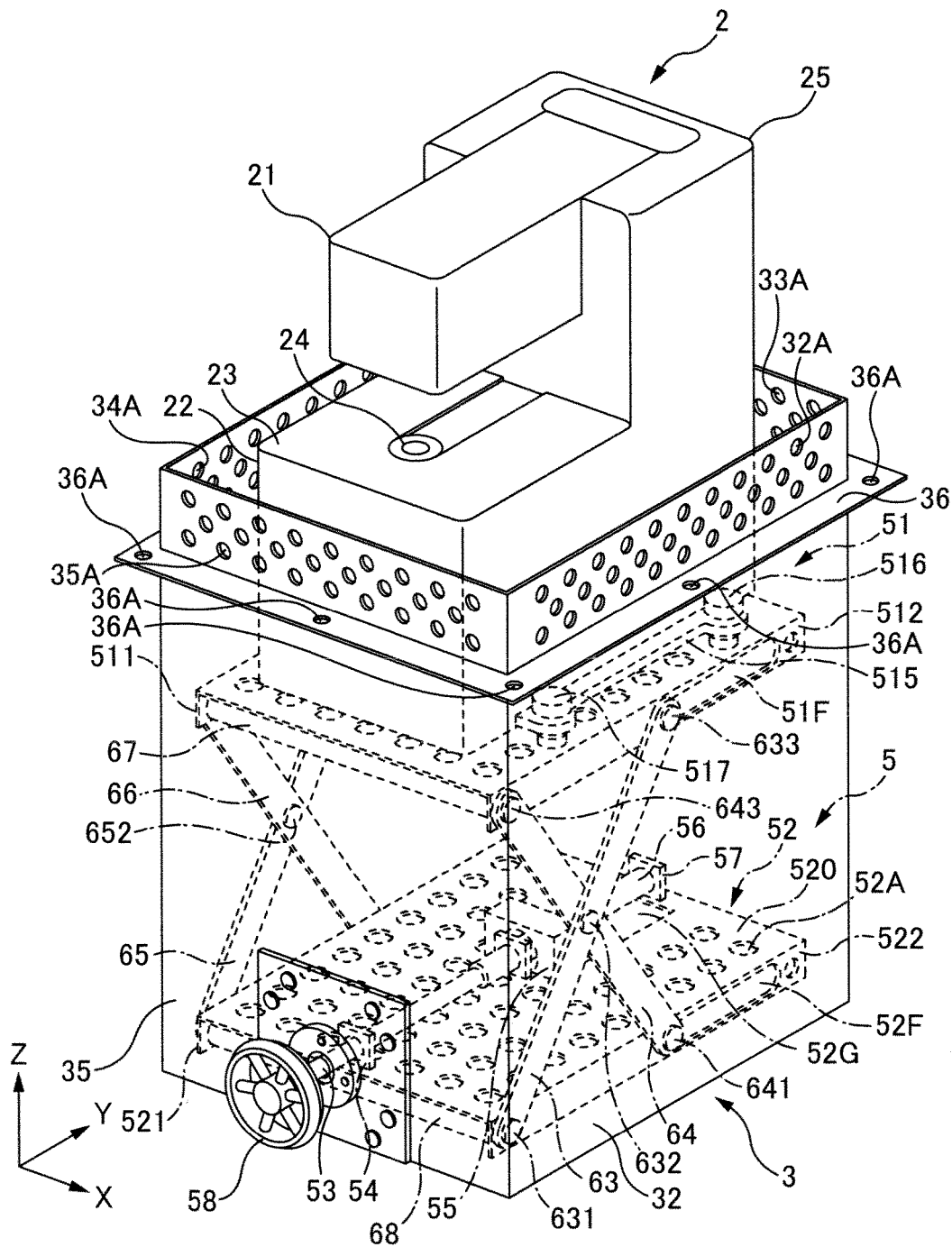
FIG. 5 is an exemplary perspective view illustrating an observation device, a storage chamber, and a lifting device according to a first embodiment of the present disclosure.

The storage chamber 3 is configured to store a lifting device 5 (FIG. 5) and an observation device 2 (hereinafter, also referred to as an "experimental device") (FIG. 5). The storage chamber 3 is formed in such a manner as to protrude downward from the bottom plate 116. Note that the details of the storage chamber 3 will be described later. It is assumed here that the predetermined height H1 is set at such a height that the centrifuge 13 and the storage chamber 3 can be provided under the bottom plate 116.

===Working Chamber===

Figure 3:
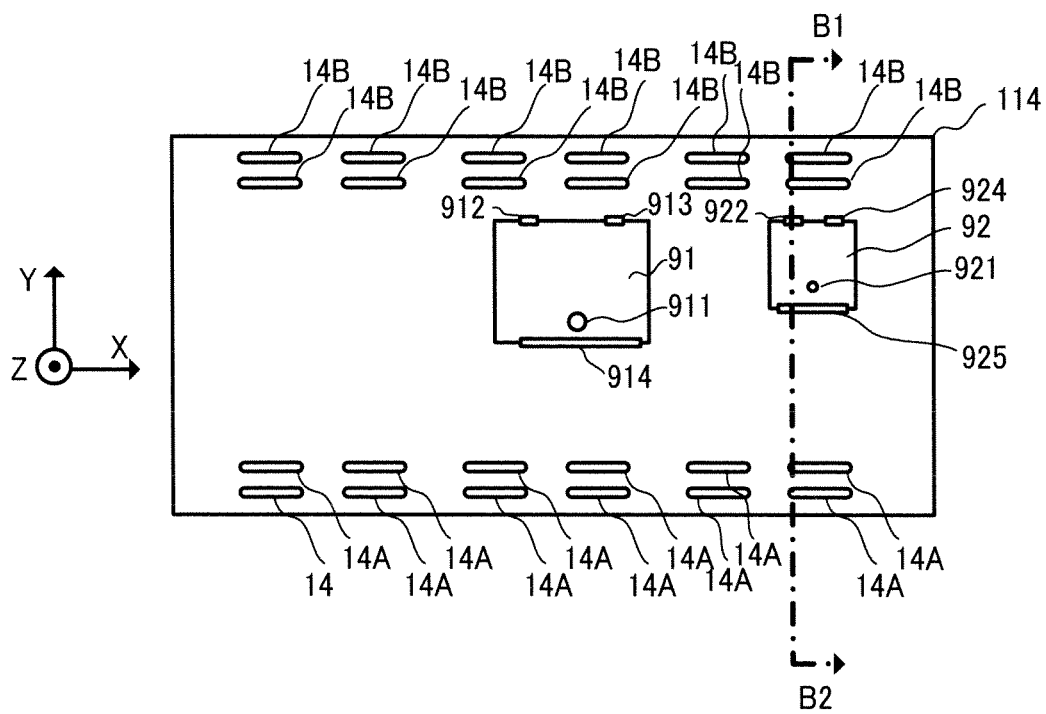
FIG. 3 is an exemplary plan view illustrating a bottom plate of a working chamber according to a first embodiment of the present disclosure.

Hereinafter, the working chamber according to an embodiment of the present disclosure will be described with reference to FIGS. 1 to 3. FIG. 3 is a plan view illustrating the bottom plate of the working chamber according to an embodiment of the present disclosure.

The working chamber 16 is a space in which work such as cell culture is performed in a state where bacterial invasion from the exterior is restrained. The working chamber 16 is a space enclosed with a work platform plate 114, partition plates 115 and 119, the top plate 112, the door 12, and the side plates 17 and 18. Note that the work platform plate 114 corresponds to a bottom plate of the working chamber 16.

The work platform plate 114 is, for example, a metal flat plate formed in a substantially rectangular shape. The length of the long side (the side along the X-axis) of the work platform plate 114 is assumed to be shorter than the length of the long side of the bottom plate 116 so that the work platform plate 114 can be provided in the interior of the chamber 10. The length of the short side (the side along the Y-axis) of the work platform plate 114 is assumed to be shorter than the length of the short side of the bottom plate 116 so that a duct 118 is formed between the partition plate 115 and the back plate 113. Note that the details of the duct 118 will be described later. The work platform plate 114 is installed above (+Z) the bottom plate 116 in the interior of the chamber 10, so as to form a duct 117 for discharging gas, such as air and sterilizing gas for sterilizing the interior of the working chamber 16 from the interior of the working chamber 16 to the exterior of the working chamber 16, between the work platform plate 114 and the bottom plate 116. The work platform plate 114 is used as, for example, such a work floor where a device and/or the like to be used for work such as cell culture is placed on the top surface of the work platform plate 114 when the work is performed in the working chamber 16. The work platform plate 114 is provided, for example, such that the top surface of the work platform plate 114 is substantially horizontal so as to facilitate the work using the top surface of the work platform plate 114. Further, the work platform plate 114 is installed in such a manner as to be easily mounted and demounted by hand.

Thus, the work platform plate 114 is demounted from the interior of the chamber 10 as needed, when the interior of the chamber 10 is cleaned, such as when wiping the bottom plate 116.

The work platform plate 114 is provided with opening and closing lids 91, 92. The opening and closing lid 91 is a member configured to open and close an opening (not shown), which is provided to the work platform plate 114 so that the centrifuge 13 arranged under the work platform plate 114 can be used in the working chamber 16. The opening and closing lid 92 is a member configured to open and close an opening 14C (FIG. 7) (hatch) provided to the work platform plate 114 so that the observation device 2 can be moved between the working chamber 16 and the storage chamber 3. Note that the details of the opening and closing lids 91, 92 will be described later.

The work platform plate 114 is provided with a plurality of holes 14A, 14B. The plurality of holes 14A, 14B are holes for gas, such as sterilizing gas and air, in the working chamber 16 to be discharged through the duct 117 and out to the exterior of the working chamber 16. A plurality of holes 14A, 14B are formed on the back plate 113 side edge (+Y) of the work platform plate 114 and on the door 12 side edge (−Y) of the work platform plate 114, respectively, for example, in belt-like forms along the long side (X-axis) of the work plat form plate 114. A plurality of holes 14A, 14B are slots in which, for example, the longitudinal direction of each of the plurality of holes 14A, 14B is, for example, along the long side of the work platform plate 114. Note that a plurality of holes 14A, 14B may be slots, in which, for example, the longitudinal direction of each of a plurality of holes 14A, 14B is, for example, along the short side (Y-axis) of the work platform plate 114. The plurality of holes 14A, 14B may be, for example, in a substantially circular form or in a substantially polygonal shape. Note that, it is conceivable that an instrument, which is used when work such as cell culture is performed in the working chamber 16, may drop from the working chamber 16 through the plurality of holes 14A, 14B to the bottom plate 116, however, since the work platform plate 114 can be mounted/demounted, the instrument can be easily collected and also cleaning can be performed there.

The partition plate 115 is, for example, a metal flat plate formed in a substantially rectangular shape, and is provided substantially parallel to the back plate 113. The length in the X-axis direction of the partition plate 115 is similar to the length of the long side of the work platform plate 114. The length in the perpendicular direction of the partition plate 115 is assumed to be shorter than the length in the perpendicular direction of the back plate 113 so that a duct 117 is formed between the work plat form plate 114 and the bottom plate 116. The partition plate 115 is positioned on the door 12 side with regard to the back plate 113 in the interior of the chamber 10 such that the duct 118 for discharging gas, such as sterilizing gas and air, from the interior of the working chamber 16 to the exterior of the working chamber 16 is formed between the partition plate 115 and the back plate 113. For example, the edge on the body 11 side of the partition plate 115 and the edge on the side opposite to the body 11 of the partition plate 115 are respectively welded to the surfaces, of the side plates 18, 17, on the working chamber 16 side.

The partition plate 119 is, for example, a metal flat plate formed in a substantially rectangular shape, for separating the duct 118 and the working chamber 16 so that gas, such as sterilizing gas and air, circulates in the working chamber 16. The length in the X-axis direction of the partition plate 119 is substantially similar to the length in the X-axis direction of the partition plate 115. The upper side edge of the partition plate 119 is welded to the top plate 112 between the position at which a pipe 71 is provided and the position at which a pipe 72 is provided. The lower side edge of the partition plate 119 is welded to the edge on the upper side of the partition plate 115. For example, the body 11 side edge of the partition plate 119 and the edge on the side opposite to the body 11 of the partition plate 119 are respectively welded to the surfaces, of the side plates 18, 17, on the working chamber 16 side. The partition plate 119 is provided in the chamber 10 in such a manner as to be inclined from the door 12 side down toward the back plate 113 side, such that a large space can be secured in the working chamber 16.

===Circulation of Gas in Working Chamber===

Hereinafter, circulation of gas in the working chamber according to an embodiment of the present disclosure will be described with reference to FIG. 2.

The chamber 10 is provided with the pipes 71, 72 and filters 711, 721.

The pipe 71 is a gas-supply pipe for supplying gas (e.g., sterilizing gas, air) from the exterior of the working chamber 16 to the interior of the working chamber 16.

The pipe 72 is a gas-discharge pipe for discharging gas (e.g., sterilizing gas, air) from the interior of the working chamber 16 to the exterior of the working chamber 16.

The filter 711 is, for example, an HEPA (High Efficiency Particulate Air) filter configured to remove impurities such as dust contained in the gas that is supplied through the pipe 71 to the interior of the working chamber 16. The filter 721 is, for example, an HEPA filter configured to remove impurities such as dust contained in the gas discharged from the interior of the working chamber 16 through the ducts 117, 118 to the exterior of the working chamber 16.

One end on the downstream side of the pipe 71 is connected to the working chamber 16. One end on the upstream side of the pipe 72 is connected to the duct 118. Note that the details of the circuit of the isolator 100 such as on the connection of the pipes 71, 72 and the like will be described later. The filters 711, 721 are provided at one downstream end of the pipe 71 and one upstream end of the pipe 72, respectively.

For example, gas supplied from upstream the pipe 71 is supplied into the working chamber 16 after the impurities thereof have been removed by the filter 711. The gas in the working chamber 16 is discharged through a plurality of holes 14A, 14B of the work platform plate 114 and the ducts 117, 118 to the pipe 72. Note that the air in the duct 118 is discharged to the pipe 72 after the impurities thereof have been removed by the filter 721.

===Circuit of Isolator===

Figure 4:
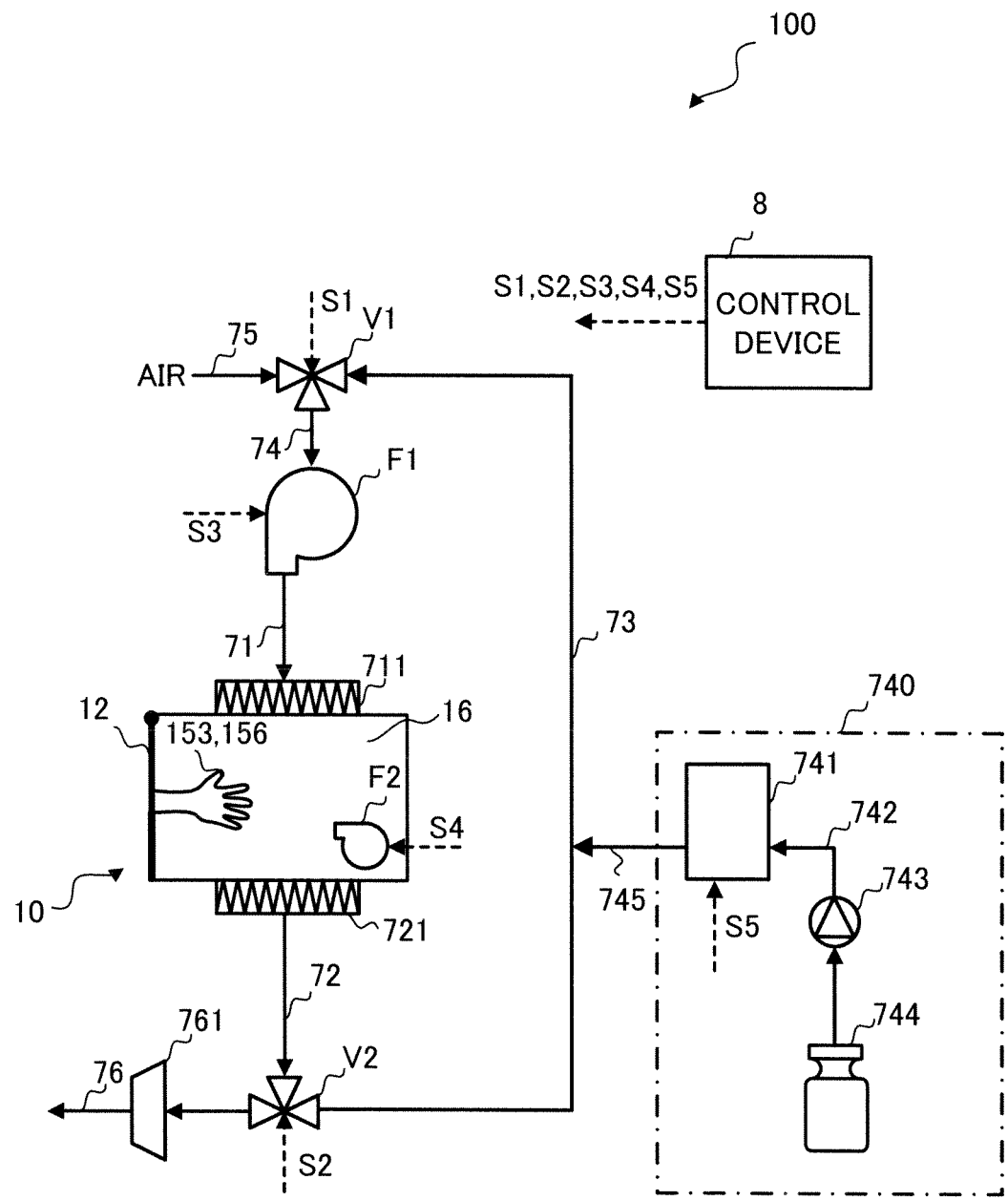
FIG. 4 is an exemplary circuit diagram of an isolator according to a first embodiment of the present disclosure.

Hereinafter, the circuit of the isolator according to an embodiment of the present disclosure will be described with reference to FIG. 4. FIG. 4 is a circuit diagram of the isolator according to an embodiment of the present disclosure.

The isolator 100 includes solenoid valves V1, V2, a blower F1, a blower F2 (fan), the chamber 10, a sterilizing gas supply unit 740, the control device 8, the pipes 71 to 76, and the filters 711, 721, 761.

The blower F1 is a device configured to circulate gas into the working chamber 16 of the chamber 10. The blower F2 is a device configured to circulate gas into the interior of the storage chamber 3 in the working chamber 16. It is assumed that the blowers F1, F2 can be switched on/off in response to the control signals S3, S4, respectively, transmitted from the control device 8. Note that the details of the blower F2 will be described later.

The valves V1, V2 are, for example, solenoid three-way valves capable of switching the gas flow path in response to the control signals S1, S2, respectively, transmitted from the control device 8. Note that the switching of the gas flow path performed by the valves V1, V2 will be described later.

A filter 761 is a device configured to reduce the concentration and render harmless the sterilizing gas contained in the gas discharged from the interior of the isolator 100 to the exterior of the isolator 100. The filter 761 is assumed to, for example, contain catalyst such as platinum, activated carbon, and the like.

The sterilizing gas supply unit 740 is configured to supply sterilizing gas for rendering the interior of the working chamber 16 and the paths into a sterile environment. The sterilizing gas supply unit 740 is assumed to be provided, for example, at the exterior of the chamber 10. Note that the sterile environment represents a dust-free/sterile environment to the highest degree possible where contamination by the materials, other than the materials necessary for the work to be performed in the working chamber 16, is restrained. The sterilizing gas supply unit 740 includes pipes 742, 745, a sterilizing gas generating device 741, a pump 743, and a container 744. The container 744 stores, for example, a sterilizing material such as hydrogen peroxide solution. The sterilizing gas generating device 741 is configured to generate sterilizing gas by pumping up through the pipe 742 the sterilizing material stored in the container 744 using the pump 743, and heating and vaporizing the pumped-up sterilizing material. The sterilizing gas generating device 741 is assumed to be controlled by a control signal S5 transmitted from the control device 8. The pipe 745 is a pipe for circulating in the working chamber 16 the sterilizing gas generated in the sterilizing gas generating device 741.

The control device 8 is configured to transmit control signals S1 to S5, for example, on the basis of the information inputted from the touch panel 111 (FIG. 1). Note that the details of the control device 8 will be described later.

The pipe 74 is connected between the valve V1 and the blower F1, the pipe 71 is connected between the blower F1 and the chamber 10, the pipe 72 is connected between the chamber 10 and the valve V2, and the pipe 73 is connected between the valve V2 and the valve V1, so that the valve V1, the blower F1, the chamber 10, and the valve V2 are connected in a loop. Note that one end of the pipe 745 is connected at the predetermined position between the two ends of the pipe 73, so that the sterilizing gas generated in the sterilizing gas generating device 741 is supplied into the pipe 73. The other end of the pipe 745 is assumed to be connected to the sterilizing gas generating device 741. One end of the pipe 75 is connected to the valve V1 so that the air in the exterior of the isolator 100 is supplied through the valve V1 to the interior of the isolator 100. The other end of the pipe 75 is assumed to be, for example, exposed to the exterior of the isolator 100. One end of the pipe 76 is connected to the valve V2 so that the gas in the interior of the isolator 100 is discharged through the valve V2 to the exterior of the isolator 100. The pipe 76 is assumed to be, for example, exposed to the exterior of the isolator 100. The filter 761 is provided at the predetermined position between the two ends of the pipe 76.

Here, the valve V1 is configured to switch the flow path of the pipes 73, 74, 75 between the first and the second flow paths on the basis of the control signal S1. Note that the first flow path is assumed to represent that the pipe 74 and the pipe 75 are connected to each other, with the pipe 73 being shut off from the pipes 74, 75. The second flow path is assumed to represent that the pipe 73 and the pipe 74 are connected to each other, with the pipe 75 being shut off from the pipes 74, 73. The valve V2 is configured to switch the flow path of the pipes 72, 73, 76 between the third and the fourth flow paths on the basis of the control signal S2. Note that the third flow path is assumed to represent that the pipe 72 and the pipe 76 are connected to each other, with the pipe 73 being shut off from the pipes 72, 76. The fourth flow path is assumed to represent that the pipe 72 and the pipe 73 are connected to each other, with the pipe 76 being shut off from the pipes 72, 73.

===Control Device===

Hereinafter, the control device according to an embodiment of the present disclosure will be described with reference to FIG. 4.

The control device 8 is configured to transmit the control signals S1 to S5, for example, on the basis of the information inputted from the touch panel 111 (FIG. 1).

For example, when a button for starting work preparation displayed on the touch panel 111 is pressed, the control device 8 transmits the control signals S1 to S5 so that a sterilization process and a substitution process are performed by the isolator 100. Note that the sterilization process represents, for example, that sterilizing gas is circulated through the interior of the working chamber 16 and the paths so as to render the interior of the working chamber 16 and the paths in a sterile environment. The substitution process represents, for example, that the sterilizing gas in the interior of the working chamber 16 and the paths is substituted with the air in the exterior of the isolator 100, thereby discharging the sterilizing gas in the interior of the working chamber 16 and the paths to the exterior of the isolator 100.

For example, when the sterilization process is performed, the control device 8 transmits the control signal S1 for switching to the second flow path, the control signal S2 for switching to the fourth flow path, the control signals S3, S4 for respectively turning on the blowers F1 and F2, and the control signal S5 for generating sterilizing gas. In this case, the sterilizing gas generated in the sterilizing gas generating device 741 is circulated in the order of the pipe 73, the valve V1, the pipe 74, the blower F1, the pipe 71, the filter 711, the working chamber 16, the filter 721, the pipe 72, and the valve V2. Thus, the interior of the working chamber 16 and the paths are sterilized by the sterilizing gas.

For example, when the substitution process is performed, the control device 8 transmits the control signal S1 for switching to the first flow path, the control signal S2 for switching to the third flow path, the control signals S3, S4 for respectively turning on the blowers F1, F2, the control signal S5 for stopping generation of the sterilizing gas. In this case, the sterilizing gas generating device 741 stops supplying the sterilizing material contained in the container 744 to the sterilizing gas generating device 741, which is performed by the pump 743, and stops heating the sterilizing material. The air exterior of the isolator 100 is supplied through the pipe 75, the valve V1, the pipe 74, the blower F1, the pipe 71, and the filter 711, into the working chamber 16. The air containing sterilizing gas in the working chamber 16 is discharged through the filter 721, the pipe 72, the valve V2, the filter 761, and the pipe 76, to the exterior of the isolator 100.

===Observation Device===

Hereinafter, the observation device according to an embodiment of the present disclosure will be described with reference to FIG. 5. FIG. 5 is a perspective view illustrating the observation device, the storage chamber, and the lifting device according to an embodiment of the present disclosure. Note that the lifting device 5 and the observation device 2 each are in a state where a part thereof cannot be seen, but is indicated by dashed lines.

The observation device 2 is, for example, an inverted phase-contrast microscope configured to observe an observation target (not shown) such as a human cell and the like. The observation device 2 includes a body 25 and a support member 515.

The body 25 includes an upper unit 21 and a lower unit 22. An irradiation device (not shown), configured to irradiate an observation target contained in a container with phase-contrast illumination is housed in the upper unit 21. In the lower unit 22, for example, an objective lens (not shown) or the like for observing the observation target, irradiated with the phase-contrast illumination, is housed immediately below an observation window 24 on an observation surface 23.

The support member 515 is a member for supporting the body 25. The support member 515 is provided with leg components 516, 517 whose lower ends have attached spherical components (not shown), which are casters for supporting the body 25 in a freely movable manner. The support member 515 is provided on a surface on the +X side of the body 25. Note that a support member (not shown) (hereinafter referred to as "the other support member") having a structure similar to that of the support member 515 is provided on the surface on the −X side of the body 25.

===Storage Chamber===

Figure 6:
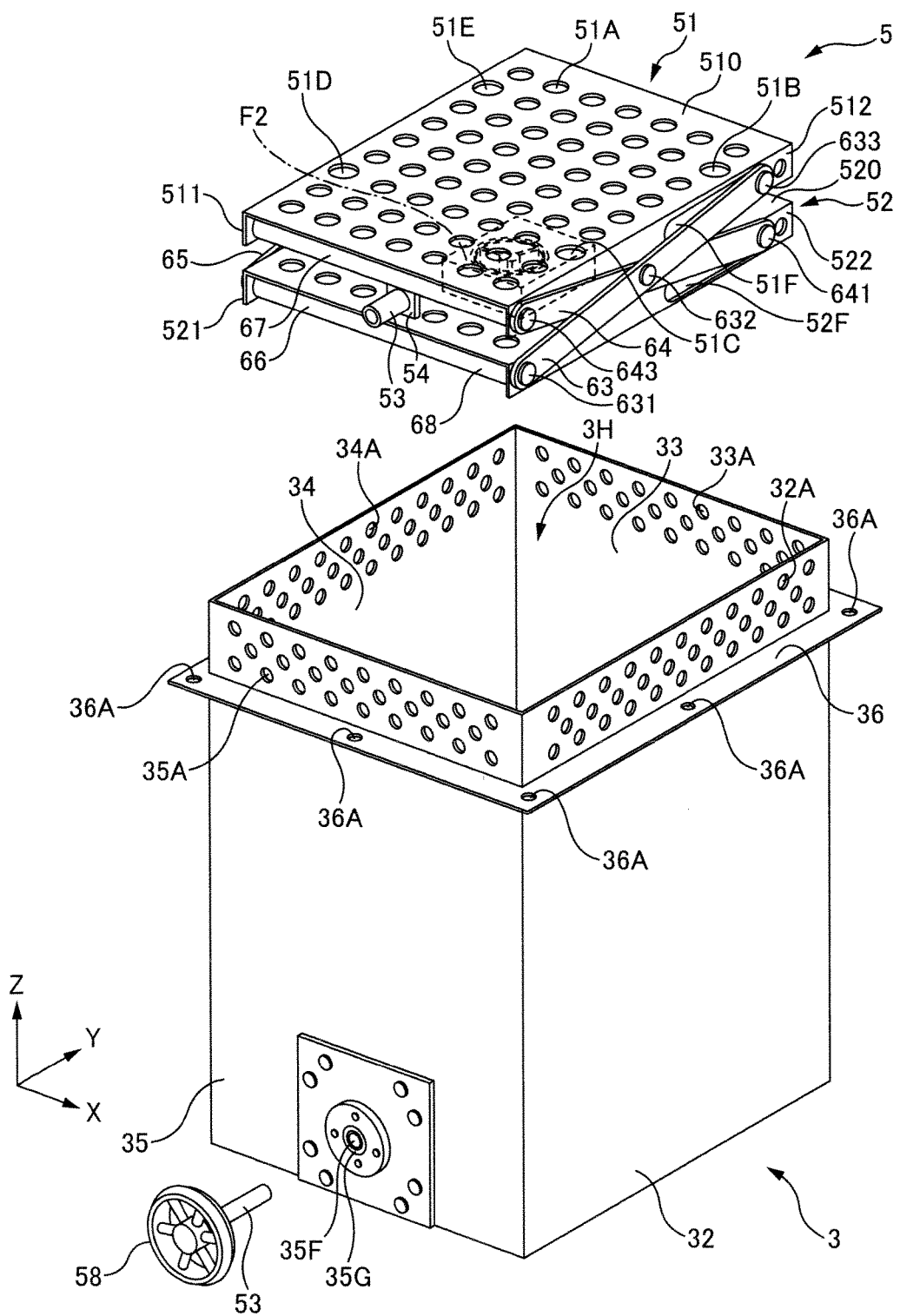
FIG. 6 is an exemplary perspective view illustrating a storage chamber and a lifting device according to a first embodiment of the present disclosure.
Figure 7:
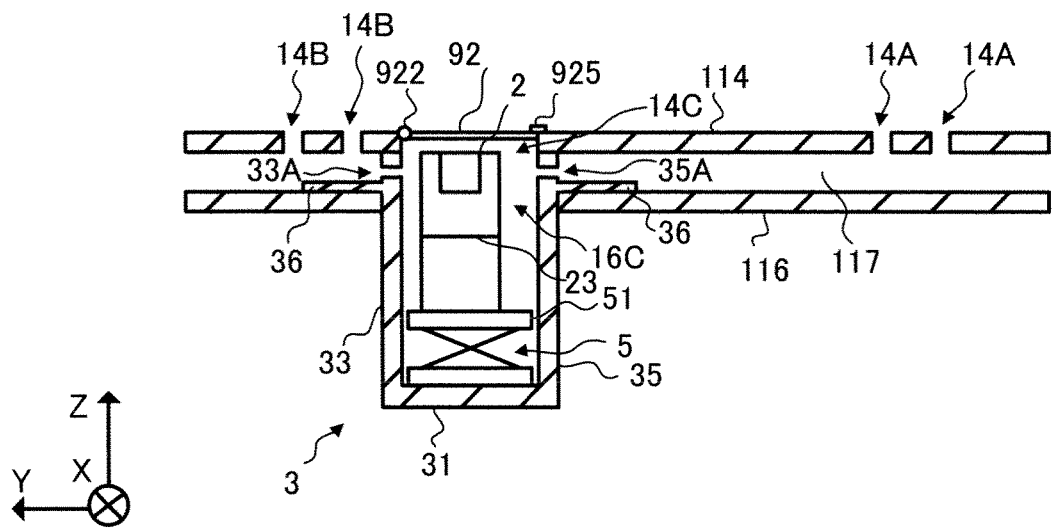
FIG. 7 is an exemplary cross-sectional view of a part of an isolator according to a first embodiment of the present disclosure.

Hereinafter, the storage chamber according to an embodiment of the present disclosure will be described with reference to FIG. 1 and FIGS. 5 to 7. FIG. 6 is a perspective view illustrating the storage chamber and the lifting device according to an embodiment of the present disclosure. Note that a shaft 53 in FIG. 6 is illustrated in a state of being divided at a predetermined position in the longitudinal direction of the shaft 53. FIG. 7 is a cross-sectional view of a part of the isolator according to an embodiment of the present disclosure when viewed from a section line B1-B2 toward the +X side in FIG. 3. Note that FIG. 7 illustrates the work platform plate 114, the bottom plate 116, the storage chamber 3, the observation device 2, and the lifting device 5.

The storage chamber 3 is configured to, for example, store the observation device 2 in the interior thereof, and is formed in a substantially rectangular box shape. The storage chamber 3 includes an opening 3H on the upper side of the storage chamber 3, so that the observation device 2 and the lifting device 5, which will be described later, can be stored from above the storage chamber 3 into the interior of the storage chamber 3. The interior of the storage chamber 3 comes into communication through the opening 3H with the interior of the chamber 10 in a state where airtightness is maintained, so that bacterial invasion from the exterior of the storage chamber 3 is restrained. The storage chamber 3 includes a bottom plate 31, side plates 32 to 35, and a flange 36.

The bottom plate 31 is, for example, a metal flat plate in a substantially rectangular shape to form the substantially horizontal bottom of the storage chamber 3. The side plates 32 to 35 are, for example, metal flat plates in a substantially rectangular shape to form side surfaces along the perpendicular direction (Z-axis) of the storage chamber 3.

The side plate 32 forms a side surface on one side (+X) of the storage chamber 3. The side plate 34 forms a side surface on the other side (−X) that opposes the side plate 32 in the storage chamber 3. The side plate 35 forms a side surface on the front side (−Y), to which a handle 58 (manual lever) is mounted, in the storage chamber 3. The side plate 33 forms a side surface on the rear side (+Y) that opposes the side plate 35 in the storage chamber 3. The side plates 32, 34 are of a similar shape, and the side plates 35, 33 are also of a similar shape. The lengths in the Y-axis direction of the side plates 32, 34 are similar to the length in the depth direction of the bottom plate 31. The lengths in the X-axis direction of the side plates 35, 33 are similar to the length in the X-axis direction of the bottom plate 31. The lengths in the perpendicular direction (Z-axis) of the side plates 32 to 35 are similar to one another. A plurality of holes 32A to 35A are respectively formed, to the side plates 32 to 35, above the position at which the flange 36 is mounted. Note that the details of the flange 36 and a plurality of holes 32A to 35A will be described later.

The lower edges of the side plates 32 to 35 are, for example, welded to one edge, a rear edge, the other edge, and a front edge in the bottom plate 31, respectively. Each pair of a front edge of the side plate 32 and one edge of the side plate 35, a front edge of the side plate 34 and the other edge of the side plate 35, the rear edge of the side plate 32 and one edge of the side plate 33, and the rear edge of the side plate 34 and the other edge of the side plate 33 is, for example, welded to each other. The interior of the storage chamber 3 and the exterior of the storage chamber 3 are separated by the bottom plate 31 and the side plates 32 to 35.

The flange 36 is a metal member for mounting the storage chamber 3 to the chamber 10. The flange 36 is a substantially horizontal plate, which is provided on the external surfaces of the side plates 32 to 35 in such a manner as to surround the storage chamber 3 from the outside. The flange 36 is, for example, welded to the external surfaces of the side plates 32 to 35 such that the upper portions of the side plates 32 to 35 protrude above the flange 36 by a predetermined length. Note that the details of the predetermined length will be described later. In the flange 36, a plurality of screw holes 36A are provided at a plurality of locations including the four corners in the flange 36.

The bottom plate 116 of the chamber 10 (FIG. 7) is provided with an opening 16C for mounting the storage chamber 3 to the chamber 10. The storage chamber 3 is fit from above the bottom plate 116 into the bottom plate 116, such that the storage chamber 3 protrudes downward. Note that the storage chamber 3 is assumed to fit into the opening 16C in a state where the work platform plate 114 has been demounted from the working chamber 16. When the storage chamber 3 is fit into the opening 16C, the undersurface of the flange 36 abuts against the periphery of the opening 16C at the top surface of the bottom plate 116. The storage chamber 3 is mounted to the chamber 10, for example, by securing the flange 36 to the chamber 10 by screws. As a result, a space is formed to protrude downward from the opening 16C of the bottom plate 116 of the chamber 10, and the chamber 10 and the storage chamber 3 come in communication with each other through the opening 3H.

Note that the top surface of the bottom plate 116 is assumed to be, for example, provided with female screws at the positions opposing the screw holes 36A. That is, the storage chamber 3 is integrated into the chamber 10 by being mounted to the chamber 10. Note that a seal material such as rubber sealing may be provided between the undersurface of the flange 36 and a part, opposing the flange 36, of the top surface of the bottom plate 116, so that the interior of the storage chamber 3 and the interior of the chamber 10 are maintained airtight when the storage chamber 3 is mounted to the chamber 10 by screws. Further, the undersurface of the flange 36 may be welded to a part, opposing the flange 36, of the top surface of the bottom plate 116 so that the interior of the storage chamber 3 and the interior of the chamber 10 are reliably maintained airtight. Thereafter, the work platform plate 114 is mounted to the interior of the chamber 10.

The work platform plate 114 is provided with the opening 14C at a position opposing the opening 16C of the bottom plate 116 when the work platform plate 114 is mounted to the interior of the chamber 10. The size of the opening 14C is assumed to be substantially similar to the size of the opening 16C.

Here, the predetermined length on the upper side from the flange 36 is set, for example, to be equal to the distance in the perpendicular direction between the work platform plate 114 and the bottom plate 116 when the storage chamber 3 is mounted to the chamber 10. Thus, parts on the upper side of the side plates 32 to 35 protrude above from the upper side of the bottom plate 116 toward the work platform plate 114 in such a manner as to traverse the duct 117. On this occasion, the upper ends of the side plates 32 to 35 may abut against the undersurface of the work platform plate 114. At this time, the duct 117 and the storage chamber 3 are separated by the side plates 32 to 35, and also the position of the opening 3H of the storage chamber 3 substantially coincides with the position of the opening 14C of the work platform plate 114. Thus, the storage chamber 3 is formed to protrude downward from the opening 14C of the work platform plate 114 in such a manner that a part of the bottom plate of the working chamber 16 is recessed, and the working chamber 16 and the storage chamber 3 are in communication with each other through the opening 14C.

Further, the side plates 32 to 35 avoid an instrument or liquid, which has dropped through the holes 14A, 14B of the work platform plate 114 to the bottom plate 116, from dropping further into the storage chamber 3. Further, the plurality of holes 32A to 35A provided to the side plates 32 to 35 are holes for allowing the sterilizing gas in the duct 117 to pass therethrough, and are provided at the position apart and above from the bottom plate 116. Further, the size of the holes 32A to 35A is set to the size comparable to the holes 14A, 14B of the work platform plate 114.

===Lifting Device===

Figure 8:
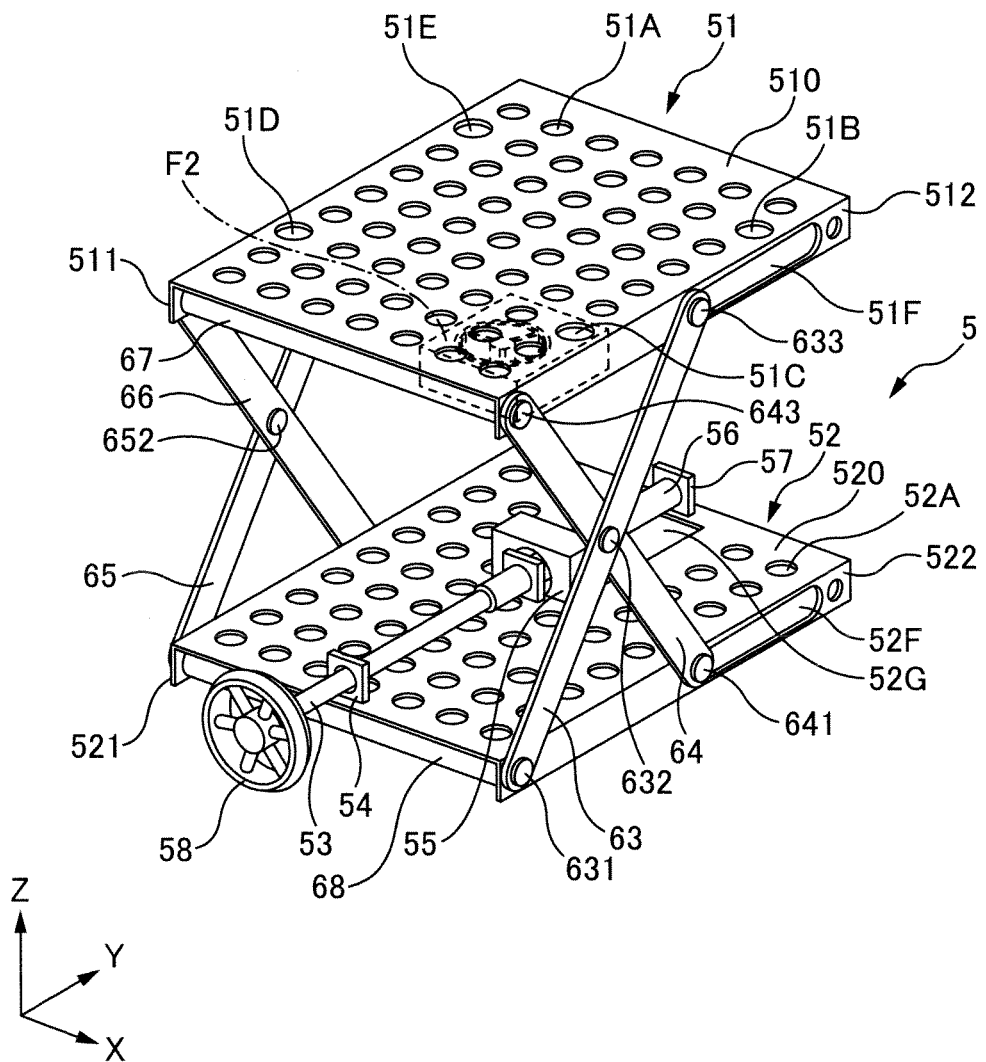
FIG. 8 is an exemplary perspective view illustrating a lifting device according to a first embodiment of the present disclosure.

Hereinafter, the lifting device according to an embodiment of the present disclosure will be described with reference to FIGS. 5, 6 and 8. FIG. 8 is a perspective view illustrating the lifting device according to an embodiment of the present disclosure.

The lifting device 5 is a device to lift/lower the observation device 2, for example, along the perpendicular direction (Z-axis) The lifting device 5 includes a mounting table 51, a supporting table 52, a handle 58, shafts 53, 56, arms 63 to 66, and a driving member 55.

The observation device 2 is mounted onto the mounting table 51. The supporting table 52 supports the mounting table 51. The supporting table 52 is, for example, mounted onto the bottom plate 31 (FIG. 7) of the storage chamber 3. The arms 63 to 66 are members to connect the mounting table 51 and the supporting table 52, and lift and lower the mounting table 51. The shafts 53, 56 and the driving member 55 are members to transmit, to the arms 64, 66, the force based on the rotational driving force which is applied through the handle 58 to the shaft 53.

The mounting table 51 is formed in a shape symmetric with respect to the z-y plane passing through the center of the mounting table 51. The mounting table 51 includes a top plate 510 and side plates 511, 512.

The top plate 510 is, for example, a metal flat plate formed in a substantially rectangular shape and provided so as to be substantially horizontal. A plurality of holes 51A and fixing holes 51B, 51C, 51D, 51E are formed in the top plate 510. The fixing holes 51B, 51C, 51D, 51E are holes for fixing the observation device 2 onto the top plate 510 by inserting thereinto spherical components respectively attached to the lower ends of the leg components 516, 517 and the leg components of the other support member. The plurality of holes 51A are, for example, holes for allowing circulation of the sterilizing gas in the working chamber 16 into the interior of the storage chamber 3. Note that the plurality of holes 51A contributes to reduce the weight of the mounting table 51. Here, the blower F2 is mounted, for example, at the corner on the front side (−Y), on which the handle 58 is provided, and one side of the undersurface of the top plate 510. The blower F2 is mounted, for example, to generate an air current directed from above (+Z) and downwards (−Z). When the blower F2 is turned on, the gas above the top plate 510 is sent through the plurality of holes 51A to the lower side of the top plate 510. That is, by the blower F2, the gas such as sterilizing gas and air in the chamber 10 is circulated in the storage chamber 3.

The side plate 512 is, for example, a metal flat plate formed in a long substantially rectangular shape, so as to connect the mounting table 51 and the upper ends of the arms 63, 64. The length of the side plate 512 in the longitudinal direction is similar to the length of the top plate 510 in the direction along the longitudinal direction of the shaft 53 (depth direction along the Y-axis). Note that the side plate 511 is in a shape similar to that of the side plate 512. The side plates 511, 512 are, for example, formed by bending one edge of the top plate 510 and the other edge of the top plate 510, respectively, such that the mounting table 51 is substantially in a U-shape when viewed from the −Y side to the +Y side. The side plate 512 is provided with a slot 51F, into which a shaft (not shown) (hereinafter, referred to as "the drive shaft of the mounting table") connecting the upper end of the arm 63 and the upper end of the arm 65 is inserted. The slot 51F is, for example, formed to extend from substantially the center to the rear (+Y) end of the side plate 512 in a state where the longitudinal direction of the slot 51F is along the longitudinal direction of the side plate 512. Note that a slot (hereinafter, referred to as "the slot of the side plate 511") similar to the slot 51F is formed in the side plate 511.

The supporting table 52 is formed in a shape symmetric with respect to the z-y plane passing through the center of the supporting table 52. The supporting table 52 includes a top plate 520 and side plates 521, 522.

The top plate 520 is, for example, a metal flat plate formed in a substantially rectangular shape, and provided so as to be substantially horizontal. An opening 52G and a plurality of holes 52A are formed in the top plate 520. The plurality of holes 52A are, for example, holes for allowing circulation of the gas such as sterilizing gas and air in the working chamber 16 into the interior of the storage chamber 3. Note that the plurality of holes 52A contributes to reduce the weight of the supporting table 52. The opening 52G is formed substantially in the center on the rear side of the top plate 520. Note that the details of the opening 52G will be described later.

The side plate 522 is, for example, a metal flat plate formed in a long substantially rectangular shape, so as to connect the supporting table 52 and the lower ends of the arms 63, 64. The length of the side plate 522 in the longitudinal direction is similar to the length of the top plate 520 in the depth direction. Note that the side plate 521 is in a shape similar to that of the side plate 522. The side plates 521, 522 are, for example, formed by bending one edge of the top plate 520 and the other edge of the top plate 520, respectively, such that the supporting table 52 is substantially in a U-shape when viewed from the −Y side to the +Y side. The side plate 522 is provided with a slot 52F, into which a shaft (not shown) (hereinafter, referred to as "the drive shaft of the supporting table") connecting the lower end of the arm 64 and the lower end of the arm 66 is inserted. The slot 52F is, for example, formed to extend from substantially the center to the rear end of the side plate 522 in a state where the longitudinal direction of the slot 52F is along the longitudinal direction of the side plate 522. Note that a slot (hereinafter, referred to as "the slot of the side plate 521") similar to the slot 52F is formed in the side plate 521. Note that the drive shaft of the supporting table, the drive shaft of the mounting table, the arms 63 to 66, and the driving member 55 are equivalent to a drive mechanism.

Each of a pair of the arm 63 and the arm 64 and a pair of the arm 65 and the arm 66 is a pair of members for connecting the mounting table 51 and the supporting table 52 and lifting and lowering the mounting table 51. The arm 63 and the arm 64 support the side plate 512 of the mounting table 51, and the arm 65 and the arm 66 support the side plate 511 of the mounting table 51. The arms 63 to 66 are in a long flat plate shape similar to one another. The arms 63, 64 are mounted to one side of the mounting table 51 and the supporting table 52, such that the arms 63, 64 intersect each other at substantially the center thereof. The substantial centers of the arms 63, 64 are pivotally coupled by a coupling member 632 so that the arms 63, 64 can be pivotally moved in relation with each other about the rotating shaft along the X-axis direction at the position at which the arm 63 and the arm 64 intersect each other.

The lower end of the arm 63 is pivotally coupled to one end of a shaft 68 by a coupling member 631 so that the arm 63 is pivotally moved about the shaft 68. Note that the shaft 68 is assumed to be provided at the front side (−Y) end of the supporting table 52 in a state where the longitudinal direction of the shaft 68 is along the X-axis. The upper end of the arm 63 is pivotally coupled to one end of the drive shaft of the mounting table by a coupling member 633, so that the arm 63 is pivotally moved about the drive shaft of the mounting table. Note that the drive shaft of the mounting table is assumed to be inserted into the slot 51F and the slot of the side plate 511, in a state where the longitudinal direction of the drive shaft of the mounting table is along the X-axis.

The upper end of the arm 64 is pivotally coupled to one end of a shaft 67 by a coupling member 643, such that the arm 64 is pivotally moved about the shaft 67. Note that the shaft 67 is assumed to be provided at the front side end of the mounting table 51 in a state where the longitudinal direction of the shaft 67 is along the X-axis. The lower end of the arm 64 is pivotally coupled to one end of the drive shaft of the supporting table by a coupling member 641, such that the arm 64 is pivotally moved about the drive shaft of the supporting table. Note that the drive shaft of the supporting table is assumed to be inserted into the slot 52F and the slot of the side plate 521, in a state where the longitudinal direction of the drive shaft of the supporting table is along the X-axis.

Note that similar to the arms 63, 64, the arms 65, 66 are mounted to the side plates 511, 521, which are respectively on the other side of the mounting table 51 and the supporting table 52.

The shafts 53, 56 are mounted by mounting members 54, 57 in substantially the center on the supporting table 52, in a state where the longitudinal direction of the shafts 53, 56 are along the Y-axis. Note that the shafts 53, 56 are assumed to be mounted so as to be rotated about the central axis of the shafts 53, 56 which are along the longitudinal direction of the shafts 53, 56. The rear end of the shaft 53 and the front end of the shaft 56 are detachably coupled to each other. The front end of the shaft 56 is assumed to be, for example, formed in a pipe shape. The rear end of the shaft 53 is assumed to be formed in such a tapered shape that, for example, the diameter thereof increases with distance from the rear toward the front, so that the shafts 53, 56 are fit each other when the rear end of the shaft 53 is inserted into the pipe of the front end of the shaft 56. The handle 58 for providing a rotational driving force to the shaft 53 is mounted to the front end of the shaft 53. The driving member 55 is a member configured to be moved along the longitudinal direction of the shaft 56 on the basis of the rotational driving force transmitted from the shaft 56. The driving member 55 is coupled, through the opening 52G, to the drive shaft of the supporting table. Note that the length in the depth direction of the opening 52G is assumed to be, for example, similar to the length of the slot 52F in the depth direction, which is the length by which the drive shaft of the supporting table is moved along the depth direction.

For example, in the case where the handle 58 is rotated in a clockwise direction (direction C1) when viewed from the front side to the rear side, the driving member 55 is assumed to be moved from the front side to the rear side in the longitudinal direction of the shaft 56. At this time, the drive shaft of the supporting table coupled to the driving member 55 is moved from the front side to the rear side. Thus, the mounting table 51 is moved downward. On the other hand, for example, in the case where the handle 58 is rotated in a counterclockwise direction (direction C2) when viewed from the front side to the rear side, the driving member 55 is assumed to be moved from the rear side to the front side along the longitudinal direction of the shaft 56. At this time, the drive shaft of the supporting table coupled to the driving member 55 is moved from the rear side to the front side. Thus, the mounting table 51 is moved upward.

Here, the side plate 35 of the storage chamber 3 is provided with a hole 35F (FIG. 6) through which the shaft 53 is inserted from the front side into the interior of the storage chamber 3. The hole 35F is provided with a seal material 35G, such as an O-ring and the like, so that the interior of the storage chamber 3 is maintained airtight when the shaft 53 is inserted from the front side toward the rear side. For example, in the case where the shaft 53 is detached from the shaft 56, the lifting device 5 can be stored from the opening 3H into the interior of the storage chamber 3, and also the lifting device 5 can be taken out from the interior of the storage chamber 3. That is, the lifting device 5 is detachably arranged in the storage chamber 3.

===Opening and Closing Lid===

Figure 9:
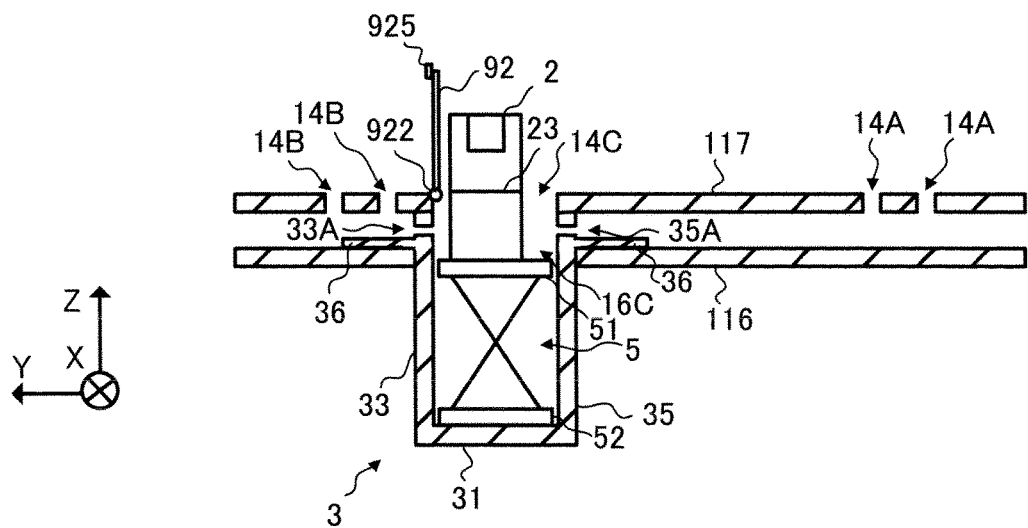
FIG. 9 is an exemplary cross-sectional view of a part of an isolator in a state where an observation device has been lifted according to a first embodiment of the present disclosure.

Hereinafter, the opening and closing lid according to an embodiment of the present disclosure will be described with reference to FIGS. 3, 7 and 9. FIG. 9 is a cross-sectional view of apart of the isolator in a state where the observation device according to an embodiment of the present disclosure has been lifted, when viewed from the section line B1-B2 toward the +X side in FIG. 3. Note that FIG. 9 illustrates the work platform plate 114, the bottom plate 116, the storage chamber 3, the observation device 2, and the lifting device 5.

The opening and closing lid 92 is a lid configured to open and close the opening 14C through which the observation device 2 is moved between the working chamber 16 and the storage chamber 3. The opening and closing lid 92 is, for example, a thin metal plate formed in a substantially rectangular shape. The opening and closing lid 92 is mounted to the top surface of the work platform plate 114 by hinges 922, 924. The opening and closing lid 92 is provided with a hole 921 which is to be a grip when the opening and closing lid 92 is opened and closed about the rotating shaft along the X-axis of the hinges 922, 924. The opening and closing lid 92 is provided with a stopper 925 for avoiding the opening and closing lid 92 from being pivotally moved downward about the rotating shaft along the X-axis of the hinges 922, 924 when the opening and closing lid 92 is under load from above. Note that the opening and closing lid 91 has a structure similar to that of the opening and closing lid 92.

The opening and closing lid 92 is opened, for example, when the observation device 2, stored in the storage chamber 3, is used in the working chamber 16. At this time, the observation device 2 can be moved from the storage chamber 3 to the working chamber 16. On the other hand the opening and closing lid 92 is closed, for example, when the observation device 2 is not used in the working chamber 16 and the observation device 2 is stored in the storage chamber 3. In such a case, the opening and closing lid 92 closes the opening 14C to become a part of the work platform plate 114, thereby securing a wide work space in the working chamber 16. That is, the opening and closing lid 92 is positioned substantially in the same plane as the work platform plate 114 of the working chamber 16 when the opening 14C is closed.

===Operation===

Figure 10:
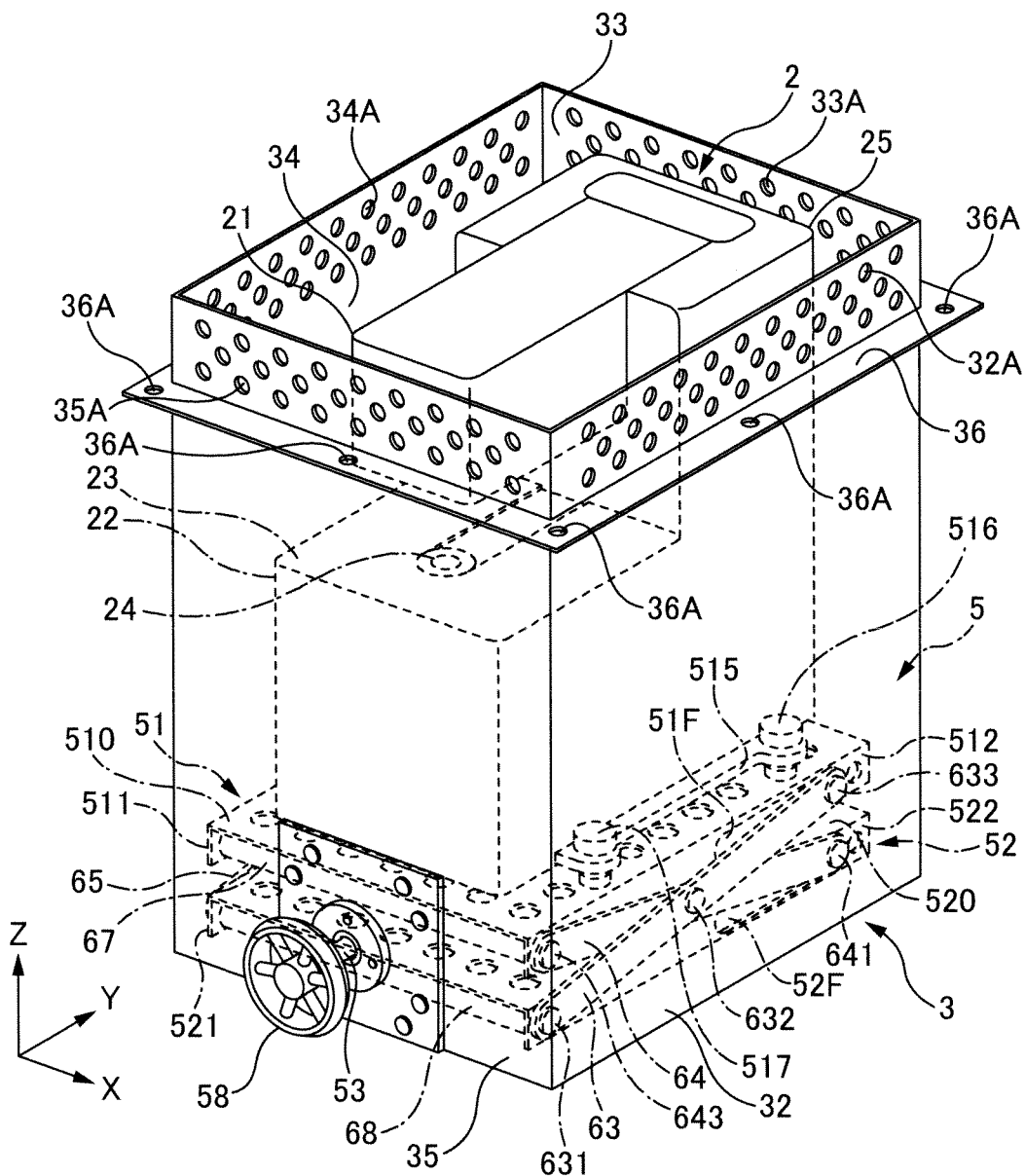
FIG. 10 is an exemplary perspective view illustrating an observation device and a lifting device in a state of being stored in a storage chamber according to a first embodiment of the present disclosure.

Hereinafter, an operation of the isolator according to an embodiment of the present disclosure will be described with reference to FIGS. 2, 4, 5, 7, 9 and 10. FIG. 10 is a perspective view illustrating the observation device and the lifting device in a state of being stored in the storage chamber according to an embodiment of the present disclosure. Note that the lifting device 5 and the observation device 2 are in a state where a part thereof cannot be seen, but is indicated by dashed lines.

The operation of the isolator 100 will be described, for example, by separating it into the case where the observation device 2, stored in the storage chamber 3, is used to perform work in the working chamber 16 and the case where the observation device 2 in the working chamber 16 is stored in the storage chamber 3 after the work is finished.

<Case Where the Observation Device 2 Stored in the Storage Chamber 3 is Used to Perform Work in the Working Chamber 16>

A worker who performs work in the working chamber 16, for example, moves the observation device 2 from the storage chamber 3 to the working chamber 16, and then pushes a button for starting work preparation displayed in the touch panel 111.

The worker opens the opening and closing lid 92, and thereafter rotates the handle 58 in the direction C2. By the rotational driving force in the direction C2 applied from the handle 58 to the shafts 53, 56, the drive shaft of the supporting table coupled to the driving member 55 is moved in the longitudinal direction of the shaft 56 from the rear side to the front side, thereby lifting the mounting table 51. Thus, the observation device 2 mounted on the mounting table 51 is moved from the storage chamber 3 to the working chamber 16. Note that, for example, the handle 58 may be rotated such that the height, of the observation surface 23 of the observation device 2, in the perpendicular direction is made equal to the height of the work platform plate 114 in the perpendicular direction.

Thereafter, the worker pushes the button for starting work preparation displayed on the touch panel 111. At this time, the isolator 100 performs the sterilization process and thereafter performs the substitution process.

The control device 8 (FIG. 4) transmits the control signal S1 for switching to the second flow path, the control signal S2 for switching to the fourth flow path, the control signals S3, S4 for turning on the blowers F1, F2, respectively, and the control signal S5 for generating sterilizing gas. In such a case, the sterilizing gas generated in the sterilizing gas generating device 741 circulates in the order of the pipe 73, the valve V1, the pipe 74, the blower F1, the pipe 71, the filter 711, the working chamber 16, the filter 721, the pipe 72 and the valve V2. Note that, in the chamber 10, the sterilizing gas circulates through the working chamber 16 and the ducts 117, 118. The sterilizing gas in the working chamber 16 and the duct 117 circulates also in the storage chamber 3 by the blower F2 mounted on the mounting table 51 of the lifting device 5.

Thereafter, the control device 8 transmits the control signal S1 for switching to the first flow path, the control signal S2 for switching to the fourth flow path, the control signals S3, S4 for turning on the blowers F1, F2, respectively, and the control signal S5 for stopping the generation of the sterilizing gas. In such a case, the sterilizing gas generating device 741 stops supplying the sterilizing material contained in the container 744 to the sterilizing gas generating device 741, which is performed by the pump 743, and stops heating the sterilizing material. The air in the exterior of the isolator 100 is supplied through the pipe 75, the valve V1, the pipe 74, the blower F1, the pipe 71, and the filter 711, into the working chamber 16. The air containing the sterilizing gas in the working chamber 16 is discharged through the filter 721, the pipe 72, the valve V2, the filter 761, and out from the pipe 76 to the exterior of the isolator 100. Note that, in the chamber 10, the air circulates through the working chamber 16 and the ducts 117, 118, and the sterilizing gas is discharged from the interior of the chamber 10. The air in the working chamber 16 and the duct 117 circulates in the storage chamber 3 by the blower F2, and the sterilizing gas in the storage chamber 3 is also discharged from the interior of the storage chamber 3.

<Case Where Observation Device 2 in Working Chamber 16 is Stored Into Storage Chamber 3>

A worker rotates the handle 58 in the direction C1. By the rotational driving force in the direction C1 applied from the handle 58 to the shafts 53, 56, the drive shaft of the supporting table coupled to the driving member 55 is moved along the longitudinal direction of the shaft 56 from the front side to the rear side, thereby lowering the mounting table 51. Thus, the observation device 2 mounted on the mounting table 51 is moved from the working chamber 16 to the storage chamber 3.

===Advantageous Effect and the Like===

In a conventional isolator, for example, changes over time of an observation target, such as a cultured cell and the like, can be observed in a working chamber of a chamber, using an observation device. At this time, work space may be decreased due to the observation device being housed in the chamber. Thus, consideration can be made to provide in the chamber a storage chamber for storing the observation device. Also, consideration can be made to form the storage chamber by making a dent to the back surface opposite to the front surface to which is attached gloves for performing work in the chamber, so as to secure a wide space for the working chamber. However, when the observation device is used in the working chamber, the observation device is moved from the storage chamber to the working chamber. Whereas, when the observation device is not used in the working chamber and the observation device is stored in the storage chamber, the observation device is moved from the working chamber to the storage chamber. The moving of the observation device between the working chamber and the storage chamber has to be manually done by the worker, and, for example, when the observation device is moved, the observation device may come into contact with the floor in the working chamber. At that time, the floor in the working chamber may be damaged or the observation device may be overturned and broken. Further, the damage of the floor in the working chamber or the breakage of the observation device will generate particles in the working chamber, and the particles may interfere with accurate observation of the observation target.

As described above, in the isolator 100 according to an embodiment of the present disclosure, the storage chamber 3 is formed to protrude downward in such a manner that a part of the work platform plate 114 of the working chamber 16 is recessed. The observation device 2 and the lifting device 5 to be used in the working chamber 16 are stored in the storage chamber 3. The lifting device 5 supports the observation device 2 in the storage chamber 3. When the observation device 2 is used in the working chamber 16, the lifting device 5 lifts the observation device 2 from the storage chamber 3 to the working chamber 16. When the observation device 2 is not used in the working chamber 16, the lifting device 5 lowers the observation device 2 from the working chamber 16 to the storage chamber 3. Thus, by virtue of the effective use of a space under the working chamber, an experimental device can be stored while securing the work space for the isolator. Further, the observation device 2 can be moved such that the observation device 2 and the work platform plate 114 in the working chamber 16 do not come into contact with each other, thereby avoiding damage in the working chamber 16 and breakage of the observation device 2. Thus, generation of particles can be avoided when the observation device 2 is moved from the storage chamber 3 to the working chamber 16 and vice versa. Further, since the movement of the observation device 2 is performed by the lifting device 5, the worker's load of storing the observation device 2 into the storage chamber 3 and demounting the observation device 2 from the storage chamber 3 can be reduced. Further, the storage chamber 3 is provided under the chamber 10. Thus, the isolator 100 can be installed on a relatively small installation surface.

Further, the side plates 32 to 35 forming the storage chamber 3, for example, avoids instruments and particles, which have dropped from the interior of the working chamber 16 to the duct 117, from further dropping to the interior of the storage chamber 3. Further, a plurality of holes 32A to 35A allow sterilizing gas to pass therethrough, and thus, for example, can avoid the flow of the sterilizing gas in the duct 117 from being blocked by the side plates 32 to 35 traversing the duct 117. Thus, the ducts 117, 118 and the storage chamber 3 communicating with the interior of the working chamber 16 is reliably decontaminated, thereby allowing the interior of the working chamber 16 to achieve an environment closer to a sterile environment.

Further, the work platform plate 114 in the working chamber 16 is provided with the opening and closing lid 92. When the opening and closing lid 92 is opened, the observation device 2 can be reliably moved between the working chamber 16 and the storage chamber 3 through the opening 14C. Further, when the opening and closing lid 92 is closed, the opening 14C is closed by the opening and closing lid 92. Therefore, for example, an instrument, which is used when performing work in the working chamber 16, can be placed on the top surface of the opening and closing lid 92, and thus a wide work space in the working chamber 16 can be utilized.

Further, the lifting device 5 stored in the storage chamber 3 is provided with the blower F2. Thereby, the circulation of the sterilizing gas in the storage chamber 3 and the discharge of the sterilizing gas from the storage chamber 3 can be reliably performed. Thus, the interior of the storage chamber 3 communicating with the interior of the working chamber 16 is reliably decontaminated, thereby being able to bring the interior of the working chamber 16 close to a dust-free and sterile environment.

Further, the lifting device 5 includes the mounting table 51 and the arms 63 to 66. The arms 63 to 66 are configured to lift and lower the mounting table 51, for example, on the basis of the rotational driving force applied from the shafts 53, 56. Thus, the observation device 2 can be lifted and lowered by mounting the observation device 2 onto the mounting table 51, and performing a simple operation of applying the rotational driving force to the lifting device 5. Hereby, the isolator 100 with high usability can be provided.

Further, the lifting device 5 is detachably arranged in the interior of the storage chamber 3. Thus, for example, when cleaning the isolator 100, the lifting device 5 is demounted from the storage chamber 3, thereby allowing to reliably perform cleaning of the lifting device 5 and cleaning of the interior of the storage chamber 3. Thus, the isolator 100 with high maintainability can be provided.

Further, the lifting device 5 includes the handle 58. And a rotational driving force can be manually applied to the lifting device 5 through the handle 58. Thus, for example, a worker can make fine adjustments to the lifting and lowering of the observation device 2 mounted on the lifting device 5. Thus, the isolator 100 with high usability can be provided.

Second Embodiment

In the first embodiment, a configuration in which the shaft 53 attached with the handle 58 is coupled to the shaft 56 has been described in the lifting device 5, but it is not limited thereto. For example, the shaft 53A, to which the rotational driving force is applied from the motor 82, may be coupled to the shaft 56. Hereinafter, a lifting device and a storage chamber according to an embodiment of the present disclosure will be described with reference to FIGS. 11 to 14.

Figure 11:
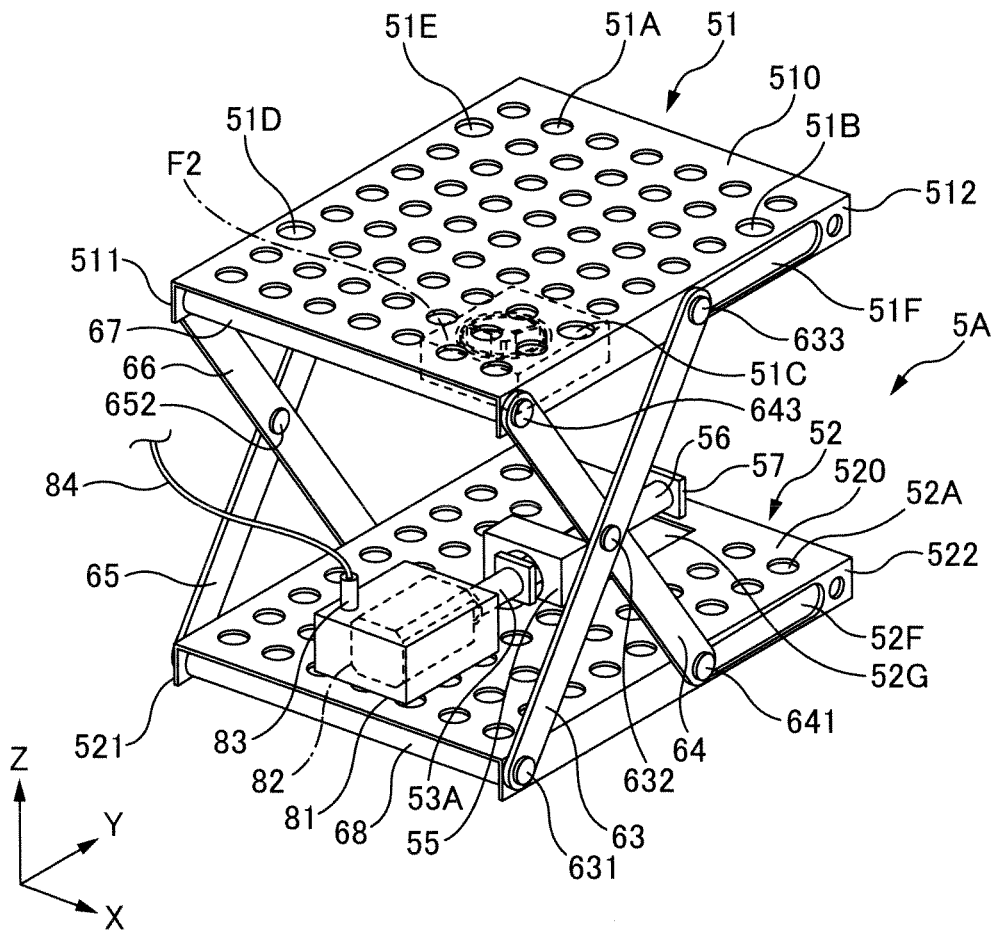
FIG. 11 is an exemplary perspective view illustrating a lifting device according to a second embodiment of the present disclosure.
Figure 12:
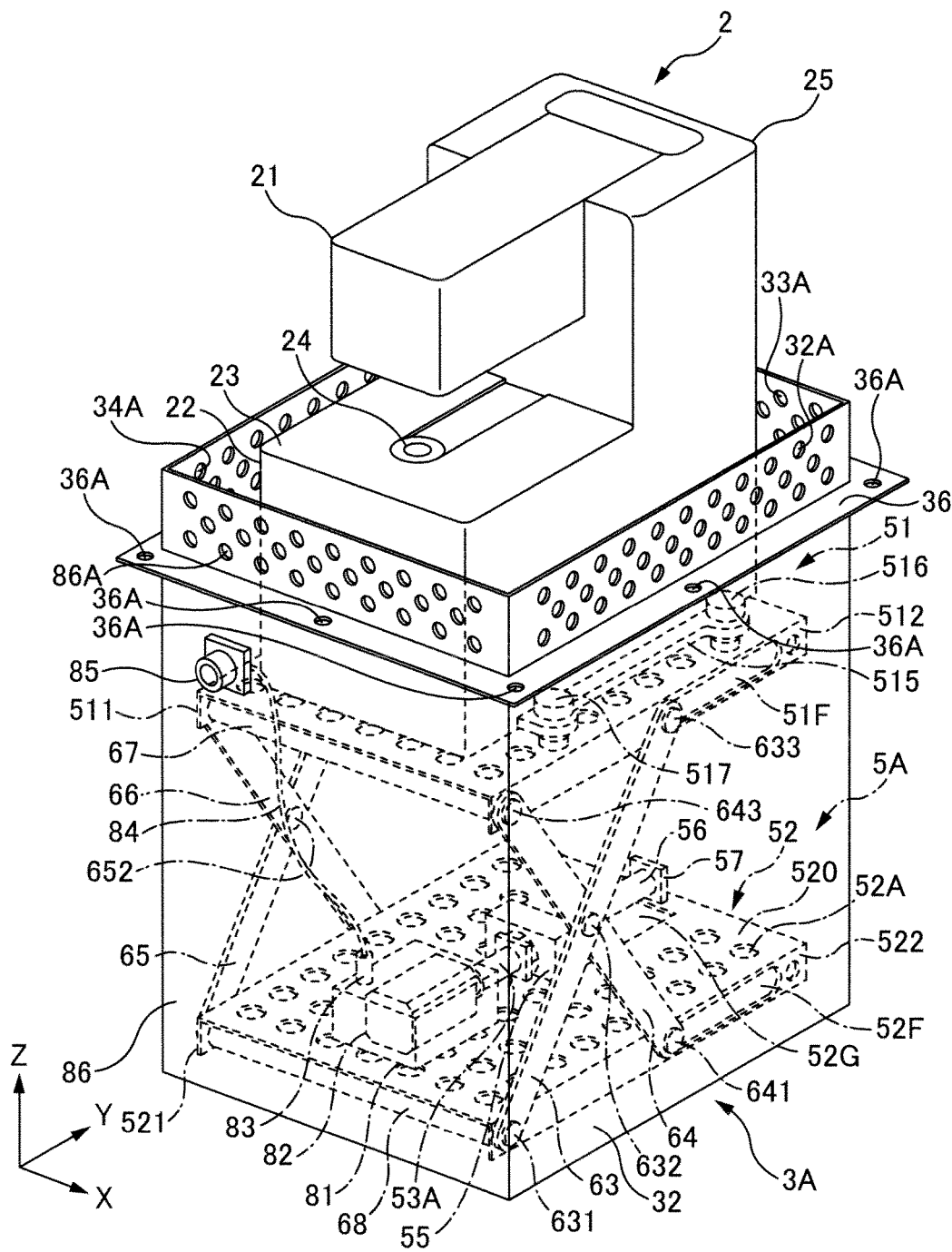
FIG. 12 is an exemplary perspective view illustrating an observation device, a storage chamber and a lifting device according to a second embodiment of the present disclosure.
Figure 13:
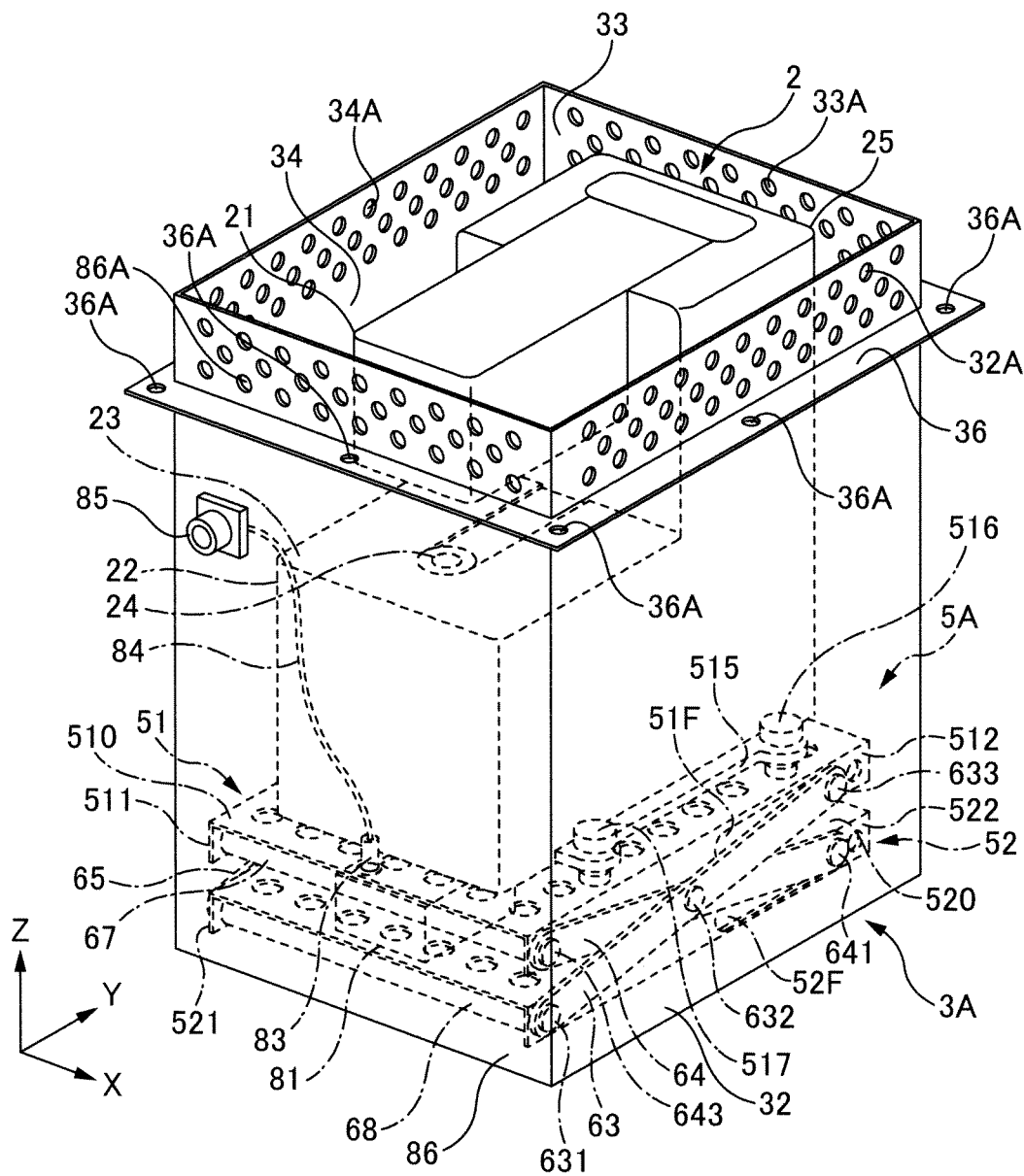
FIG. 13 is an exemplary perspective view illustrating an observation device and a lifting device in a state of being stored in a storage chamber according to a second embodiment of the present disclosure.
Figure 14:
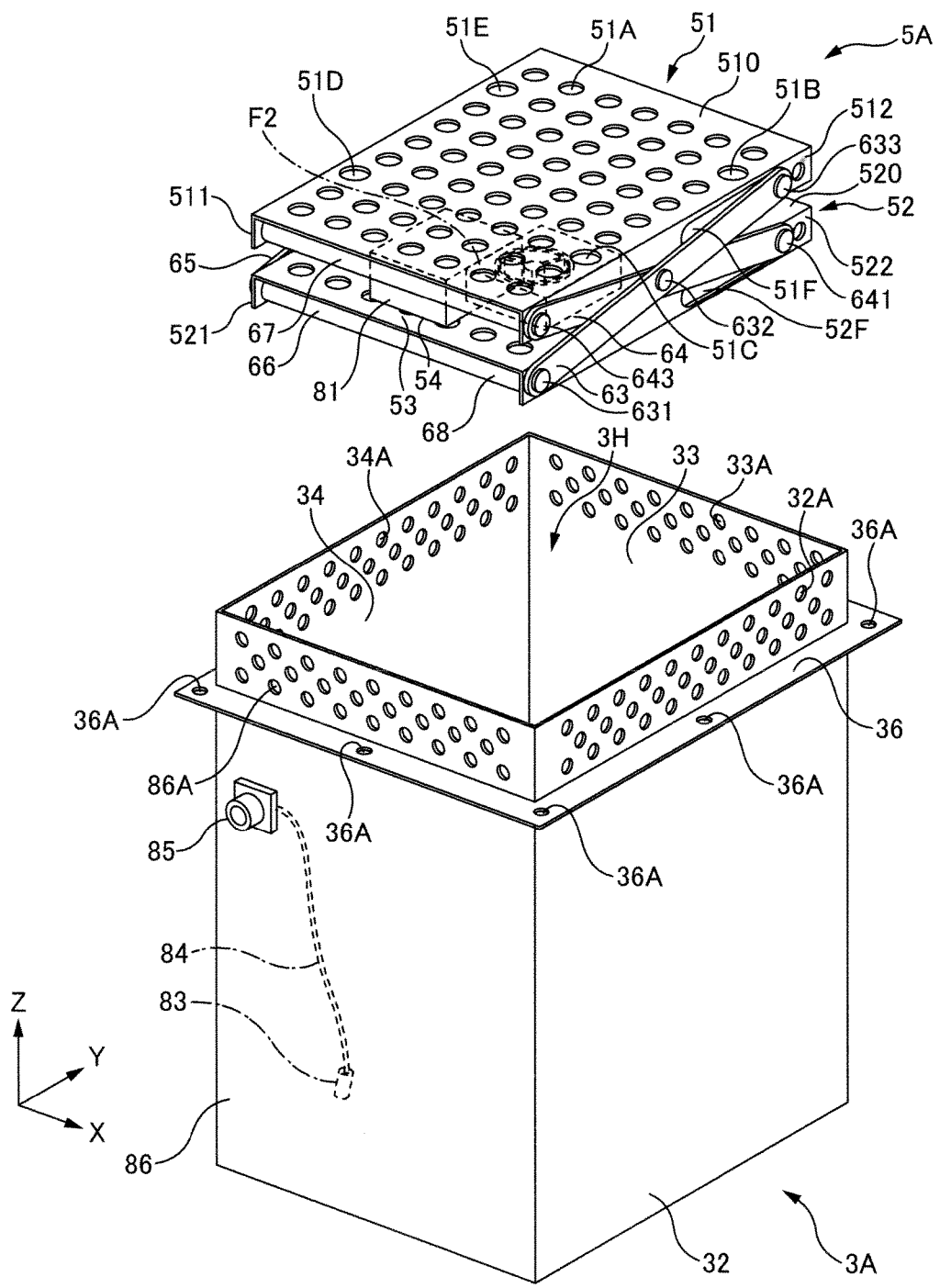
FIG. 14 is an exemplary perspective view illustrating a storage chamber and a lifting device according to a second embodiment of the present disclosure.

FIG. 11 is a perspective view illustrating the lifting device according to an embodiment of the present disclosure. Note that components similar to those illustrated in FIG. 8 are only designated by the same reference numerals and descriptions thereof are omitted. FIG. 12 is a perspective view illustrating an observation device, a storage chamber, and a lifting device according to an embodiment of the present disclosure. Note that components similar to those illustrated in FIG. 5 are only designated by the same reference numerals and the descriptions thereof are omitted. The lifting device 5A and the observation device 2 are in a state where parts thereof cannot be seen but are indicated by dashed lines. FIG. 13 is a perspective view illustrating the observation device and the lifting device in a state stored in the storage chamber according to an embodiment of the present disclosure. Note that components similar to those illustrated in FIG. 10 are only designated by the same reference numerals and descriptions thereof are omitted. Note that the lifting device 5A and the observation device 2 are in a state where parts thereof cannot be seen but are indicated by dashed lines. FIG. 14 is a perspective view illustrating the storage chamber and the lifting device according to an embodiment of the present disclosure. Note that components similar to those illustrated in FIG. 6 are only designated by the same reference numerals and descriptions thereof are omitted.

The lifting device 5A includes the motor 82 and the shaft 53A.

The shaft 53A is provided on the supporting table 52 in such a manner as to be parallel to the shaft 56. The motor 82 is attached to the front side (−Y) end of the shaft 53A so that rotational driving force is applied from the motor 82 to the shaft 53A. The rear side (+Y) end of the shaft 53A is coupled to the front side end of the shaft 56 so that the rotational driving force of the shaft 53A is transmitted to the shaft 56.

The motor 82 is a device configured to apply rotational driving force to the shaft 53A. The motor 82 is assumed to be, for example, disposed under a cover 81 formed substantially in a rectangular parallelepiped shape. The motor 82 is assumed to be configured to provide rotational driving force to the shaft 53A on the basis of a control signal inputted from the exterior of the storage chamber 3A (FIG. 12) through a conductive line 84 to the motor 82. Note that a plug 83, configured to electrically connect one end of the conductive line 84 and the motor 82, is attached to one end of the conductive line 84. Note that the plug 83 is detachably attached to a terminal (not shown), which is electrically connected to the motor 82 provided under the cover 81, so that a control signal is applied to the motor 82. For example, the plug 83 is detached (FIG. 14) when the lifting device 5A is demounted from the interior of the storage chamber 3A. The other end of the conductive line 84 is connected with a terminal 85 which is provided at the storage chamber 3A.

The storage chamber 3A includes a side plate 86. The side plate 86 forms a side surface on the front side of the storage chamber 3A. The side plate 86 is provided with the terminal 85 for inputting control signals for controlling the motor 82 from the exterior of the storage chamber 3A to the motor 82.

The control signal for controlling the motor 82 is assumed to be, for example, outputted from a control device (not shown) which is provided in the exterior of the storage chamber 3A. The control device is assumed to be configured to output control signals for controlling the rotational direction, the number of revolutions, and the rotational speed of the motor 82. The mounting table 51 of the lifting device 5A is moved upward (+Z) and downward (−Z) on the basis of rotational driving force applied from the motor 82 to the shaft 53A in response to a control signal transmitted from the control device.

As described above, the lifting device 5A includes the motor 82. A control signal is transmitted to the motor 82, thereby being able to lift and lower the observation device 2 mounted on the mounting table. The distance from the installation surface 300 to the observation device 2 can be accurately adjusted by accurately controlling the number of revolutions of the motor 82. Thus, for example, the distance from the installation surface 300 to the observation surface 23 of the observation device 2 can be made to substantially equal the distance from the installation surface 300 to the top surface of the work platform plate 114 in the working chamber 16, so as to facilitate use of the observation device 2 in the working chamber 16. Thus, the isolator with high usability can be provided. Further, for example, movement speed when the observation device 2 is moved is adjusted, to reduce the vibration caused by the movement speed when the observation device 2 is moved, thereby reliably avoiding breakage resulting from the vibration of the observation device 2.

Note that the first and second embodiments are simply for facilitating the understanding of the present disclosure and are not in anyway to be construed as limiting the present disclosure. The present disclosure may variously be changed or altered without departing from its spirit and encompass equivalents thereof.

The first embodiment describes a configuration, in which the storage chamber 3 stores the observation device 2, but it is not limited thereto. For example, the storage chamber 3 may store a device or the like configured to maintain, at a constant temperature, a reagent which is used when work such as cell culture is performed in the working chamber 16.

What is claimed is:

1. An isolator comprising:
a chamber including a working chamber in which a work is performed by a worker, and a storage chamber provided under the working chamber in communication with an opening formed in a bottom plate of the working chamber, the chamber being configured to isolate the working chamber and the storage chamber from an exterior while in a state where airtightness is maintained; and
a lift configured to support in the storage chamber an experimental device to be used in the working chamber, the lift being capable of lifting and lowering the experimental device from the storage chamber into the working chamber and from the working chamber into the storage chamber.

2. The isolator according to claim 1, wherein
the chamber includes a duct formed, at least between a bottom plate of the working chamber and a bottom plate of the chamber, to circulate in the interior of the working chamber a sterilizing gas for sterilizing an interior of the working chamber,
the duct traverses side plates of the storage chamber, and
a plurality of holes are formed in parts, traversed by the duct, in the side plates of the storage chamber, the holes allowing the sterilizing gas in the duct to pass therethrough.

3. The isolator according to claim 2, comprising:
a fan installed in the storage chamber, and configured to circulate in the storage chamber the sterilizing gas having passed through the plurality of holes.

4. The isolator according to claim 3, wherein
the lift includes
a mounting table on which the experimental device is mounted, and
a drive mechanism configured to lift and lower the mounting table on a basis of a rotational driving force.

5. The isolator according to claim 4, wherein
the lift is detachably arranged in the storage chamber.

6. The isolator according to claim 4, wherein
the lift includes a manual lever capable of applying a rotational driving force to the drive mechanism.

7. The isolator according to claim 4, wherein
the lift includes a motor capable of applying a rotational driving force to the drive mechanism.

8. The isolator according to claim 2, wherein
the lift includes
a mounting table on which the experimental device is mounted, and a drive mechanism configured to lift and lower the mounting table on a basis of a rotational driving force.

9. The isolator according to claim 8, wherein the lift is detachably arranged in the storage chamber.

10. The isolator according to claim 8, wherein the lift includes a manual lever capable of applying a rotational driving force to the drive mechanism.

11. The isolator according to claim 8, wherein the lift includes a motor capable of applying a rotational driving force to the drive mechanism.

12. The isolator according to claim 1, comprising:
an opening and closing lid capable of opening and closing an opening formed in the bottom plate of the working chamber, wherein
the opening and closing lid is positioned substantially on a same plane as the bottom plate of the working chamber when the opening is closed.

13. The isolator according to claim 12, wherein the lift includes
   a mounting table on which the experimental device is mounted, and
   a drive mechanism configured to lift and lower the mounting table on a basis of a rotational driving force.

14. The isolator according to claim 13, wherein the lift is detachably arranged in the storage chamber.

15. The isolator according to claim 13, wherein the lift includes a manual lever capable of applying a rotational driving force to the drive mechanism.

16. The isolator according to claim 13, wherein the lift includes a motor capable of applying a rotational driving force to the drive mechanism.

17. The isolator according to claim 1, wherein the lift includes
   a mounting table on which the experimental device is mounted, and
   a drive mechanism configured to lift and lower the mounting table on a basis of a rotational driving force.

18. The isolator according to claim 17, wherein the lift is detachably arranged in the storage chamber.

19. The isolator according to claim 17, wherein the lift includes a manual lever capable of applying a rotational driving force to the drive mechanism.

20. The isolator according to claim 17, wherein the lift includes a motor capable of applying a rotational driving force to the drive mechanism.

21. The isolator according to claim 1, wherein the lift is configured to lift and lower the entire experimental device from the storage chamber into the working chamber and from the working chamber into the storage chamber.

* * * * *